(12) United States Patent
Dubois

(10) Patent No.: US 11,739,192 B2
(45) Date of Patent: Aug. 29, 2023

(54) RECOVERY OF (METH) ACRYLIC RESIN BY DEPOLYMERIZATION AND HYDROLYSIS

(71) Applicant: Arkema France, Colombes (FR)

(72) Inventor: Jean-Luc Dubois, Millery (FR)

(73) Assignee: ARKEMA FRANCE, Colombes (FR)

( * ) Notice: Subject to any disclaimer, the term of this patent is extended or adjusted under 35 U.S.C. 154(b) by 73 days.

(21) Appl. No.: 17/049,735

(22) PCT Filed: Apr. 26, 2019

(86) PCT No.: PCT/FR2019/050991
§ 371 (c)(1),
(2) Date: Oct. 22, 2020

(87) PCT Pub. No.: WO2019/207264
PCT Pub. Date: Oct. 31, 2019

(65) Prior Publication Data
US 2021/0040288 A1    Feb. 11, 2021

(30) Foreign Application Priority Data
Apr. 27, 2018 (FR) ...................... 18.53708

(51) Int. Cl.
C08J 11/14 (2006.01)
C07C 51/09 (2006.01)
C07C 67/333 (2006.01)
C08J 11/16 (2006.01)

(52) U.S. Cl.
CPC ............... *C08J 11/14* (2013.01); *C07C 51/09* (2013.01); *C07C 67/333* (2013.01); *C08J 11/16* (2013.01); *C08J 2333/08* (2013.01); *C08J 2333/10* (2013.01)

(58) Field of Classification Search
CPC ...... B23B 2200/0452; B23B 2200/087; B23B 2200/286; B23B 2205/12; B23B 2250/12; B23B 27/10; B23B 27/143; B23B 27/145; B23B 27/22; B23B 29/043; B23C 2220/36; B23C 2250/12; B23C 3/30; B24B 19/02; B24B 27/033; C08J 11/14; C08J 11/16; C08J 11/22; C08J 2333/08; C08J 2333/10; C08J 2333/12; Y02W 30/62; B62K 5/02; B62K 5/10; C07C 51/09; C07C 57/04; C07C 67/333; C07C 69/54

See application file for complete search history.

(56) References Cited

U.S. PATENT DOCUMENTS

| | | | |
|---|---|---|---|
| 6,677,448 B1 * | 1/2004 | Brunelle | C07D 201/08 |
| | | | 540/539 |
| 2008/0021241 A1 * | 1/2008 | Carlson | C07C 51/44 |
| | | | 562/526 |
| 2014/0051886 A1 * | 2/2014 | Broell | C07C 51/09 |
| | | | 562/598 |

FOREIGN PATENT DOCUMENTS

| | | | |
|---|---|---|---|
| CN | 102247705 | * | 11/2011 |
| CN | 103588636 | | 2/2014 |
| DE | 19729065 | * | 1/1999 |
| EP | 1352891 | * | 10/2003 |
| TW | 201722901 | * | 7/2017 |

OTHER PUBLICATIONS

DE19729065 translation (Year: 1999).*
TW201722901 translated (Year: 2017).*
Liang et al. (Carbon Black reinforced polymethyl methacrylate (PMMA)-based composite particles: preparation, characterization, and application, J. Geophys. Eng. 14, pp. 1225-1232, published 2017) (Year: 2017).*
CN 102247705 translated (Year: 2011).*

* cited by examiner

*Primary Examiner* — Jafar F Parsa
*Assistant Examiner* — Blaine G Doletski
(74) *Attorney, Agent, or Firm* — Buchanan, Ingersoll & Rooney PC

(57) ABSTRACT

The invention relates to a process (100) for the recycling of an article based on (meth)acrylic thermoplastic polymer resin, characterized in that it comprises the following steps:
introduction (110) of the article into a system suitable for the recycling of thermoplastic polymer,
at least partial depolymerization (130) of the (meth) acrylic thermoplastic polymer resin so as to form (meth)acrylate monomers,
introduction (140) of a hydrolysis catalyst into a hydrolysis reactor,
introduction (150) of water into said hydrolysis reactor, and
conversion (160), in the hydrolysis reactor, of at least part of the (meth)acrylate monomers into (meth)acrylic acid.

The invention also relates to a system for recycling an article based on (meth)acrylic thermoplastic polymer resin.

21 Claims, 9 Drawing Sheets

RECOVERY OF (METH) ACRYLIC RESIN BY DEPOLYMERIZATION AND HYDROLYSIS

This application claims benefit, under U.S.C. § 119 or § 365 of PCT Application Number PCT/FR2019/050991, filed Apr. 26, 2019, and French Patent Application Number FR18.53708 filed Apr. 27, 2018, these documents being incorporated herein by reference.

TECHNICAL FIELD

The present invention relates generally the recycling of articles based on (meth)acrylic polymer resin and/or made of composite material based on (meth)acrylic polymer resin, in particular based on poly(methyl methacrylate).

The invention finds applications in various industrial sectors such as the environment or plastics engineering, and in particular in sectors confronted with the problems of recycling of post-consumption waste such as products at the end of their service life, or industrial waste such as defective products or scraps originating from plastics engineering operations.

PRIOR ART

In 2017, thousands of tonnes of thermoplastics were produced worldwide. The production and recycling of thermoplastics thus appear as major environmental and economic challenges, particularly the recycling of articles containing methacrylic polymers. Given the low cost of methacrylic thermoplastic polymers, their low weight and their durability, these polymers are produced in very large amount and are widely used. The accumulation of products at the end of their service life and of products derived from transformation or production processes gives rise to the problem of the recycling of said products. The products in question may comprise a methacrylic thermoplastic polymer resin and in certain cases may take the form of a composite article based on methacrylic thermoplastic polymer resin.

Recycling methods have been developed for the purpose of recycling products or articles made of methacrylic thermoplastic polymer. These methods generally make it possible to obtain monomers based on thermoplastic polymer with a view to reusing them in the manufacture of articles made of thermoplastic polymer.

Among the conventional methods for recycling articles including a methacrylic thermoplastic polymer resin, depolymerization in a bed of molten tin or lead is known. In this method, the articles are milled and are then decomposed in a molten lead/tin bed brought to a temperature generally above 400° C. However, such a process has several drawbacks. During the depolymerization, one drawback is the accumulation of solid residues at the surface of the molten metal. In the case of composites, solid residues and/or fibers accumulate continuously. This process is thus accompanied by problems of fouling of the lead/tin bed and of the reactor in which it is placed. These problems are accentuated in the case of composites since the bed of molten metal needs to be regularly freed of the residues at its surface in order to continue to extract the gaseous monomer from the reactor. Cleaning of the reactor, and of the various elements constituting the device for depolymerization on the bed of molten metal, is an additional step in the treatment of the articles which emburdens the environmental, energy and economic balance. Moreover, toxic byproducts notably derived from the cleaning steps, containing lead or tin, are generated. This contaminated waste should be appropriately processed, which entails significant associated costs. These various processes are energy-intensive and expensive. In addition, the gases derived from the depolymerization must be condensed and purified. Generally, the purification step for the purpose of isolating the monomer is complex, is accompanied by losses and the yield in terms of monomer recovery is low. This recycling process is thus unsatisfactory on the whole and is unsuitable for the processing of composites. Moreover, during the depolymerization of articles including methacrylic thermoplastic polymers, notably composite articles, a certain number of impurities that are difficult to separate from the methyl methacrylate monomer are generated, which compromises the re-use of the methyl methacrylate in an identical application.

The fluidized-bed depolymerization process is also known, in which the fluidized bed may be a bed of sand or silica placed in a fluidized-bed reactor. In this process, an article, for example based on polymethyl methacrylate resin, referred to hereinbelow as PMMA, is premilled and the milled material obtained is then introduced into the reactor containing the fluidized bed under a stream of hot gas with a temperature generally above 400° C. In this fluidized bed, the resin is rapidly heated, depolymerized and leads to the methyl methacrylate monomer, referred to hereinbelow as MMA. However, in this case also, a certain number of impurities that are difficult to separate from the methyl methacrylate monomer may be generated, which compromises the reuse of the methyl methacrylate in an identical application.

DE19729065 describes a process for the thermal depolymerization of polymethyl methacrylate to form the monomer. The described process does not comprise a step of hydrolysis of the monomer.

CN103588636 describes a process for catalyzing the hydrolysis reaction of methyl methacrylate (MMA) in order to obtain a (meth)acrylic acid. The catalyst consists of a strongly acidic cation-exchange macroporous resin which enables hydrolysis of MMA with water at a temperature of between 50 and 75° C. at atmospheric pressure and over a time of between 30 and 60 hours.

US 2004/0051886 describes a process for preparing methacrylic acid from the hydrolysis of purified methyl methacrylate derived from a process known as the acetone cyanohydrin process. The described process does not comprise a step of depolymerization of a polymer.

Thus, the conventional methods for recycling (meth) acrylic thermoplastic polymer resin in particular based on poly(methyl methacrylate) PMMA conventionally consist in depolymerizing the polymer, and generally lead to the production of monomers, such as MMA, contaminated with impurities, such as methyl isobutyrate, and/or methyl propionate, and/or methyl acrylate, and/or ethyl acrylate.

Technical Problem

The aim of the invention is thus to overcome at least one of the abovementioned drawbacks of the prior art.

The invention is notably directed toward providing a simple and efficient solution for recycling articles based on (meth)acrylic polymers. The invention is also directed toward a process for the specific depolymerization of polymer, while at the same time enabling saving in energy. The invention thus falls within a context of sustainable development and the upgrading of (meth)acrylic thermoplastic resin waste.

Brief Description of the Invention

To this end, according to a first aspect, the invention proposes a process for the recycling of an article based on (meth)acrylic thermoplastic polymer resin, characterized in that it comprises the following steps:
- introduction of the article into a system suitable for the recycling of thermoplastic polymer,
- at least partial depolymerization of the (meth)acrylic thermoplastic polymer resin so as to form (meth)acrylate monomers,
- introduction of a hydrolysis catalyst into a hydrolysis reactor,
- introduction of water into said hydrolysis reactor, and
- conversion, in the hydrolysis reactor, of at least part of the (meth)acrylate monomers into (meth)acrylic acid.

In the context of the process according to the invention, the thermoplastic polymer resin is at least partially converted into (meth)acrylic acid following hydrolysis of (meth)acrylate monomers originating from the resin. It is then possible to obtain a mixture comprising (meth)acrylic ester monomers and the corresponding (meth)acrylic acids but also impurities such as: isobutyrate, isobutyric acid and esters of butanol and of acids. The compounds of the mixture resulting from the hydrolysis according to the invention may be separated, given the differences in the physicochemical properties of the compounds present such as the boiling points, the melting points and/or the solubilities in water. Purification processes may then be performed to obtain a relatively pure solution of compound to be upgraded, for instance methacrylic acid, which is a compound of interest. In addition, the use of a catalyst makes it possible to reduce the hydrolysis temperature or is generally reflected by acceleration of the hydrolysis reaction.

According to other optional features of the recycling process:
- the hydrolysis catalyst is selected from: alumina, MgO, CaO, $Mg(OH)_2$, $Ca(OH)_2$, $Al(OH)_3$, a zeolite, an acid, a base, an amphoteric compound or a mixture of two or more of these compounds; and preferably alumina, MgO, CaO, $Mg(OH)_2$, $Ca(OH)_2$, $Al(OH)_3$, a zeolite, a base, an amphoteric compound or a mixture of two or more of these compounds,
- the recycling process according to the invention may also comprise a step of regenerating the catalyst and more particularly of the hydrolysis catalyst. This is particularly suitable when the hydrolysis catalyst is a heterogeneous catalyst. Specifically, the process may then comprise a step of placing said heterogeneous hydrolysis catalyst in contact with a regenerative substance in order to reactivate said heterogeneous hydrolysis catalyst;
- the process also includes a step of introducing a depolymerization-initiating catalyst into said system which is suitable for the recycling of thermoplastic polymer. Such a depolymerization-initiating catalyst makes it possible to induce cleavage in the polymer chain and thus to accelerate the depolymerization. The initiating catalyst is preferably introduced into a depolymerization reactor, which is advantageously different from the hydrolysis reactor;
- the depolymerization-initiating catalyst is chosen from: an organic peroxide, an inorganic peroxide or superoxide such as barium peroxide ($BaO_2$), potassium superoxide ($KO_2$), cesium superoxide ($CsO_2$), a percarbonate, a peroxyhydrate compound, salts thereof and also a mixture thereof. Depolymerization-initiating catalysts that may be mentioned include hydrogen peroxide ($H_2O_2$), azobisisobutyronitrile (AIBN), sodium (or potassium or magnesium or calcium) carbonate peroxyhydrate ($2Na_2CO_3 \cdot 3H_2O_2$), ammonium carbonate peroxyhydrate (($NH_4)_2CO_3 \cdot H_2O_2$), urea peroxide ($CO(NH_2)_2 \cdot H_2O_2$), sodium sulfate peroxyhydrate ($2Na_2SO_4 \cdot H_2O_2 \cdot 2H_2O$), complexes of $H_2O_2$ and of inorganic salts, the peroxyhydrate of poly(vinylpyrrolidone) polymer ($PVP \cdot H_2O_2$), persulfates, permanganates, perborates, and peroxyhydrates of phosphate salts. The depolymerization-initiating catalyst is preferably sodium percarbonate;
- the concentration of depolymerization-initiating catalyst is such that the mole ratio between the concentration of depolymerization-initiating catalyst and the concentration of (meth)acrylic thermoplastic polymer present in the article introduced is between 0.001 and 10;
- the depolymerization is performed in the hydrolysis reactor. In this case, the depolymerization may advantageously be performed before the hydrolysis. It then takes place in the absence of water. Alternatively, the depolymerization and hydrolysis steps are consecutive and in two different reactors.
- the process also includes a distillation step that is suitable for generating a mixture enriched in (meth)acrylic acid. This separation step is notably possible due to the differences in boiling point of the various compounds present;
- the process also comprises a crystallization step that is suitable for generating a mixture enriched in (meth)acrylic acid. A mixture enriched in (meth)acrylic acids is more particularly a composition including a majority of (meth)acrylic acids. Specifically, the process according to the invention makes it possible to obtain a mixture including one or more (meth)acrylic acids and impurities and, due to the differences in melting point between the (meth)acrylic acids and the impurities, it is possible by crystallization to isolate the one or more (meth)acrylic acids. In addition, the purification method by crystallization is simple and inexpensive to perform;
- the article to be recycled is made of composite material based on (meth)acrylic thermoplastic polymer resin and a reinforcer;
- the process also comprises a step of recovering heat, preferably heat stored by the reinforcer. This heat recovery may be advantageously used in the recycling process to produce steam, to heat the recycling system reactor and/or to keep the pipes at a given temperature.

The invention also relates to a system for recycling an article based on (meth)acrylic thermoplastic polymer resin. This system is mainly characterized in that it comprises:
- a means for introducing the article into said system,
- a hydrolysis reactor,
- a means for introducing water into said hydrolysis reactor,
- a means for introducing a hydrolysis catalyst into said hydrolysis reactor, and
- a heating means, which is preferably suitable for inducing the depolymerization and hydrolysis of at least a part of the article to be recycled.

According to other features of the system:
- the system includes one of the following devices: a reactive extruder, a fluidized-bed device, a circulating fluidized-bed device, a mixer-conveyor; a rotating blending device, a stirred rotating oven or a plate reactor.

It also includes a device for regenerating hydrolysis catalyst. The hydrolysis catalyst regenerating device is preferably connected to the reactor or forms an integral part of said hydrolysis reactor.

It includes one or more purification devices. Purification devices such as distillation and/or crystallization devices will make it possible in combination with the hydrolysis reactor to form a relatively pure fraction of (meth)acrylic acid which can then be upgraded.

It includes a device that is suitable for heat recovery. The presence of a heat recovery device is particularly advantageous in the context of a recycling system including a hydrolysis reactor, given that it may be configured to recover the heat accumulated by the remaining solid fraction (non-depolymerized or non-depolymerizable fraction such as glass fibers) in a depolymerization step so as to allow a hydrolysis step.

The device suitable for heat recovery is capable of using the recovered heat to heat water and/or to maintain at least a part of the system according to the invention at a temperature above 100° C.

BRIEF DESCRIPTION OF THE DRAWINGS

Other features and advantages of the invention will become apparent on reading the following description given for illustrative purposes and without any implied limitation, with reference to the appended figures, which depict.

DESCRIPTION OF THE INVENTION

Figure 1:
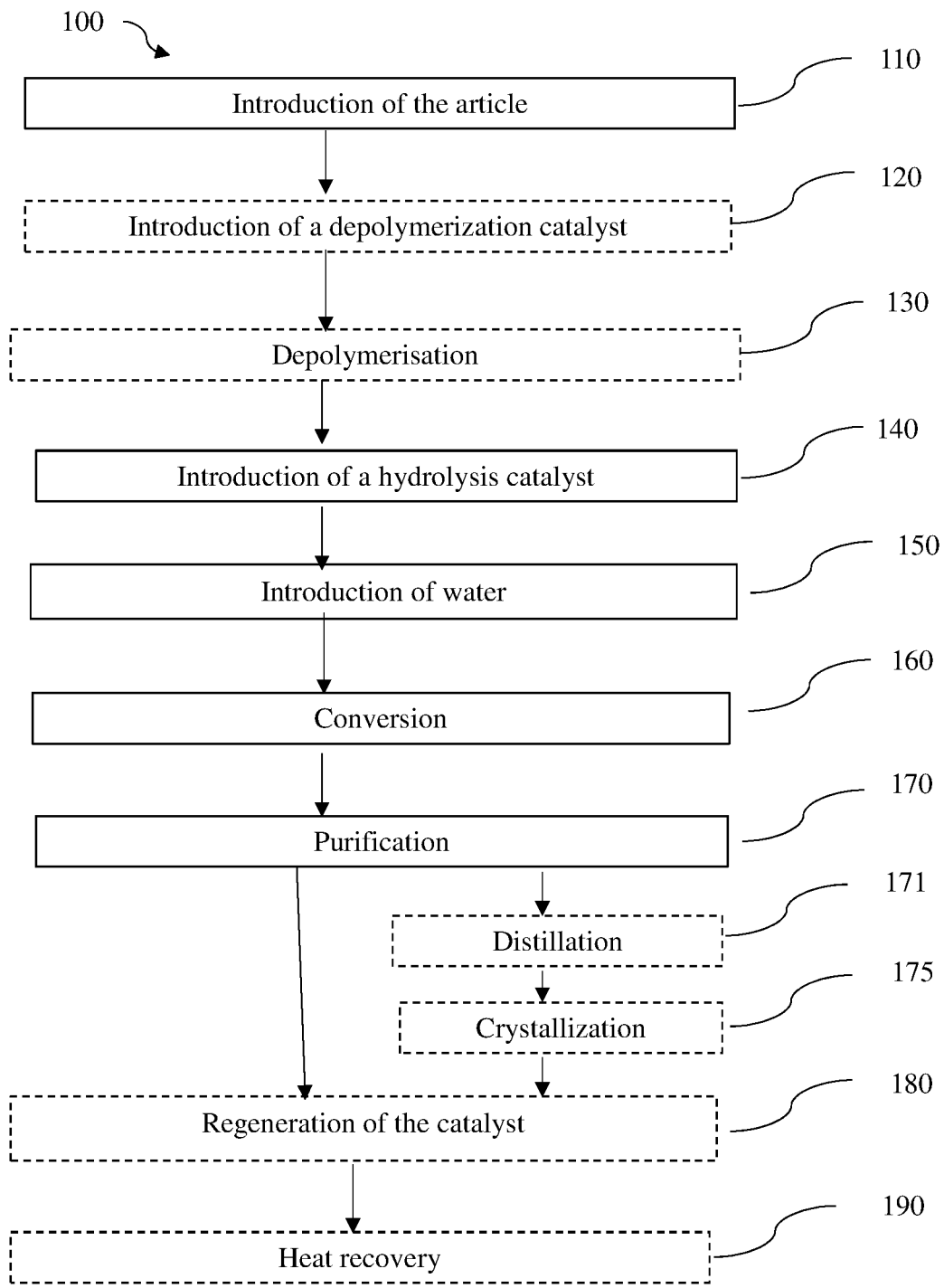
FIG. 1, a diagram showing steps of the recycling process according to one embodiment, the dotted steps are optional, FIG. 2, a scheme of a recycling system according to the invention, FIG. 3, a scheme of a twin-screw extruder for performing the process according to one embodiment, FIG. 4, a scheme of a fluidized-bed device for performing the process according to another embodiment, and FIG. 5, a scheme of a recycling system, according to one embodiment, incorporating a heat recovery device, FIG. 6, a schematic representation of a hydrolysis catalyst regenerating device, FIG. 7a, a scheme of a hydrolysis catalyst regenerating device inside the recycling device according to one embodiment and FIG. 7b, a scheme of a hydrolysis catalyst regenerating device outside the recycling device according to one embodiment, FIG. 8, a scheme of a hydrolysis catalyst regenerating device coupled to a reactor combining hydrolysis and depolymerization according to one embodiment.

In the rest of the description, the term "polymer resin" means a material which serves as binder. The "resin" includes polymers and/or oligomers. Thus, a "(meth)acrylic polymer resin" relates to any type of acrylic and methacrylic compounds, polymers, oligomers or copolymers. However, it would not constitute a departure from the scope of the invention if the (meth)acrylic polymer resin comprised up to 10% by weight, preferably less than 5% by weight, of other nonacrylic monomers chosen, for example, from the following group: butadiene, isoprene, styrene, substituted styrene, such as α-methylstyrene or tert-butylstyrene, cyclosiloxanes, vinylnaphthalenes and vinylpyridines.

The term "monomer" means a molecule which can undergo a polymerization.

The term "polymerization" as used relates to the process for converting a monomer or of a mixture of monomers into a polymer.

The term "polymer" means either a copolymer or a homopolymer. A "copolymer" is a polymer grouping together several different monomer units and a "homopolymer" is a polymer grouping together identical monomer units.

The term "(meth)acrylic thermoplastic polymer" means a polymer essentially comprising (meth)acrylic monomers which represent at least 50% by weight or more of the (meth)acrylic polymer. The (meth)acrylic monomers are chosen, for example, from methyl methacrylate, ethyl methacrylate, methyl acrylate, ethyl acrylate, acrylic acid, methacrylic acid, n-butyl acrylate, isobutyl acrylate, n-butyl methacrylate, isobutyl methacrylate, cyclohexyl acrylate, cyclohexyl methacrylate, isobornyl acrylate and isobornyl methacrylate, and mixtures thereof. Poly(methyl methacrylate) (PMMA) is a particular example of a (methacrylic) polymer obtained by polymerization of a methyl methacrylate monomer. For the purposes of the invention, the term "PMMA" denotes homo- and copolymers of methyl methacrylate (MMA), the weight ratio of MMA in the PMMA preferably being at least 70% by weight for the MMA copolymer.

The term "(meth)acrylic acids" means methacrylic acid or acrylic acid.

The term "copolymer based on methyl methacrylate" means a copolymer containing at least one methyl methacrylate monomer. For example, a copolymer based on methyl methacrylate may be a copolymer comprising at least 70%, preferably 80%, advantageously 90% by weight of MMA in the PMMA.

The term "base monomer" means the most predominant monomer unit constituting a polymer. Thus, in PMMA, the base monomer is MMA.

The term "polymer of reduced molecular mass" means a polymer, derived from an initial polymer or starting polymer, and whose molecular mass is less than the molecular mass of the starting polymer. The weight-average molecular mass may be measured by size exclusion chromatography.

For the purposes of the invention, the term "composite" means a multi-component material comprising at least two immiscible components, in which at least one component is a polymer and the other component may be, for example, a reinforcer.

The term "reinforcer" means a non-depolymerizable or gasifiable solid material such as a "fibrous reinforcer" or a "mineral filler" which remain at the end of the treatment.

The term "fibrous reinforcer" means a plurality of fibers, unidirectional rovings or a continuous filament mat, fabrics, felts or nonwovens which may be in the form of strips, webs, braids, strands or parts.

The term "mineral fillers" means all pulverulent fillers, for example quartz, marble, silica, aluminum hydroxide or $TiO_2$.

Contrary to the polymerization process, which is a process of transforming monomer(s) into a polymer, the term "depolymerization" denotes herein a process in which an initial polymer P1 is transformed into a polymer P2 of reduced molecular mass, or even into its base monomer(s).

The term "partial depolymerization" means herein a depolymerization in which the polymer is partially converted into monomer, for example without the action of water (e.g. steam). This generally results in a mixture of polymer and of monomer, the polymers having a lower average molecular mass than before the partial depolymerization. In contrast, total depolymerization corresponds to the depolymerization of substantially all of the (meth)acrylic thermoplastic polymer resin.

The term "hydrolysis catalyst" refers to a species which catalyses the hydrolysis reaction of the (meth)acrylic monomer.

The term "depolymerization-initiating catalyst" means a compound which can induce radical-mediated cleavage of the polymer chain.

The term "reactive extruder" means a reactor including one or more endless screws serving notably for blending the polymers introduced into said reactor.

The term "regenerator" or "regeneration" refers to a device in which the reactivation of a hydrolysis catalyst can take place by means of the introduction of a regenerative substance. Such a hydrolysis catalyst, for example alumina, can be reactivated under an oxidative atmosphere in order to remove the carbon-based residues which become deposited on its surface.

The term "crystallization" means the separation by selective solidification of a compound.

In the description hereinbelow of the various embodiments and in the appended figures, the same reference numerals are used to denote the same elements or similar elements.

The invention relates to a process for recycling an article based on (meth)acrylic thermoplastic polymer resin.

The (meth)acrylic thermoplastic polymer resin may be a resin based on acrylic homopolymers and copolymers, poly (alkyl acrylate) or polyalkyl (meth)acrylates, for instance poly(methyl methacrylate), and mixtures thereof.

In particular, the (meth)acrylic thermoplastic polymer resin may be a poly(methyl methacrylate) resin, also written as PMMA. Notably, such a PMMA may be the product sold by the company Arkema under the name Altuglas®.

The assembly of (meth)acrylic monomers, in a polymerization process, leads to the formation of a polymer having a linear or crosslinked chain of higher molecular mass than that of the base monomer.

The article may be, for example, made of composite material, i.e. based on (meth)acrylic thermoplastic polymer resin intimately bonded to a reinforcer. A reinforcer may be, for example, a mineral filler such as quartz, marble, calcium phosphate, chalk or carbon black.

A reinforcer may also be a fibrous reinforcer comprising an assembly of one or more fibers, generally several fibers, said assembly being able to have different forms and dimensions; one-dimensional, two-dimensional or three-dimensional. The one-dimensional form corresponds to linear long fibers. The two-dimensional form corresponds to nonwoven reinforcers or fibrous mats or woven rovings or bundles of fibers, which may also be braided. The three-dimensional form corresponds, for example, to stacked or folded nonwoven fibrous reinforcers or fibrous mats or stacked or folded bundles of fibers or mixtures thereof; an assembly of the two-dimensional form in the third dimension. The fibers may be discontinuous or continuous. When the fibers are continuous, the assembly thereof forms fabrics.

The origins of the fibers constituting the fibrous reinforcer may be natural or synthetic. Natural materials that may be mentioned include plant fibers, wood fibers, animal fibers or mineral fibers. Plant fibers are, for example, sisal, jute, hemp, linen, cotton, coconut, and banana fibers. Animal fibers are, for example, wool or fur. The mineral fibers may also be chosen from glass fibers, in particular of type E, R or S2, basalt fibers, carbon fibers, boron fibers or silica fibers. Synthetic materials that may be mentioned include polymer fibers chosen from thermosetting polymer fibers, thermoplastic polymers or mixtures thereof. The polymer fibers may consist of polyamide (aliphatic or aromatic), polyester, polyvinyl alcohol, polyolefins, polyurethanes, polyvinyl chloride, polyethylene, unsaturated polyesters, epoxy resins and vinyl esters.

Figure 3:
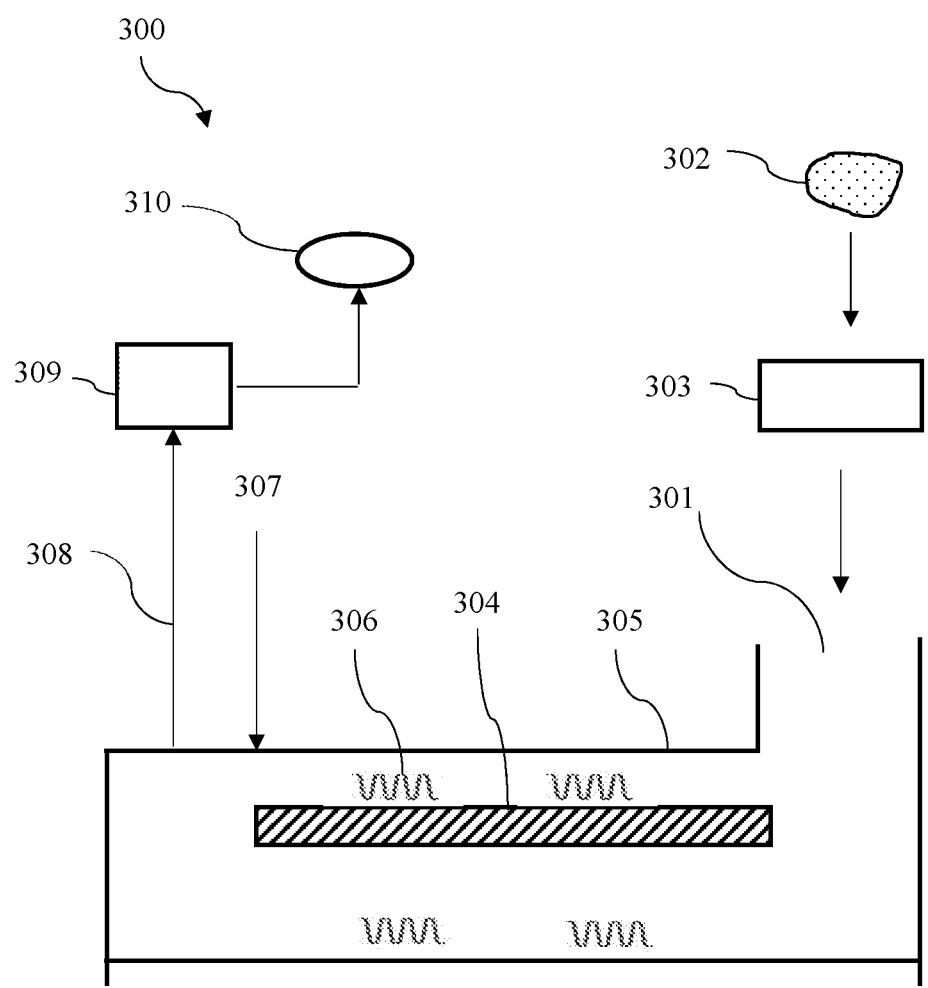
Figure 4:
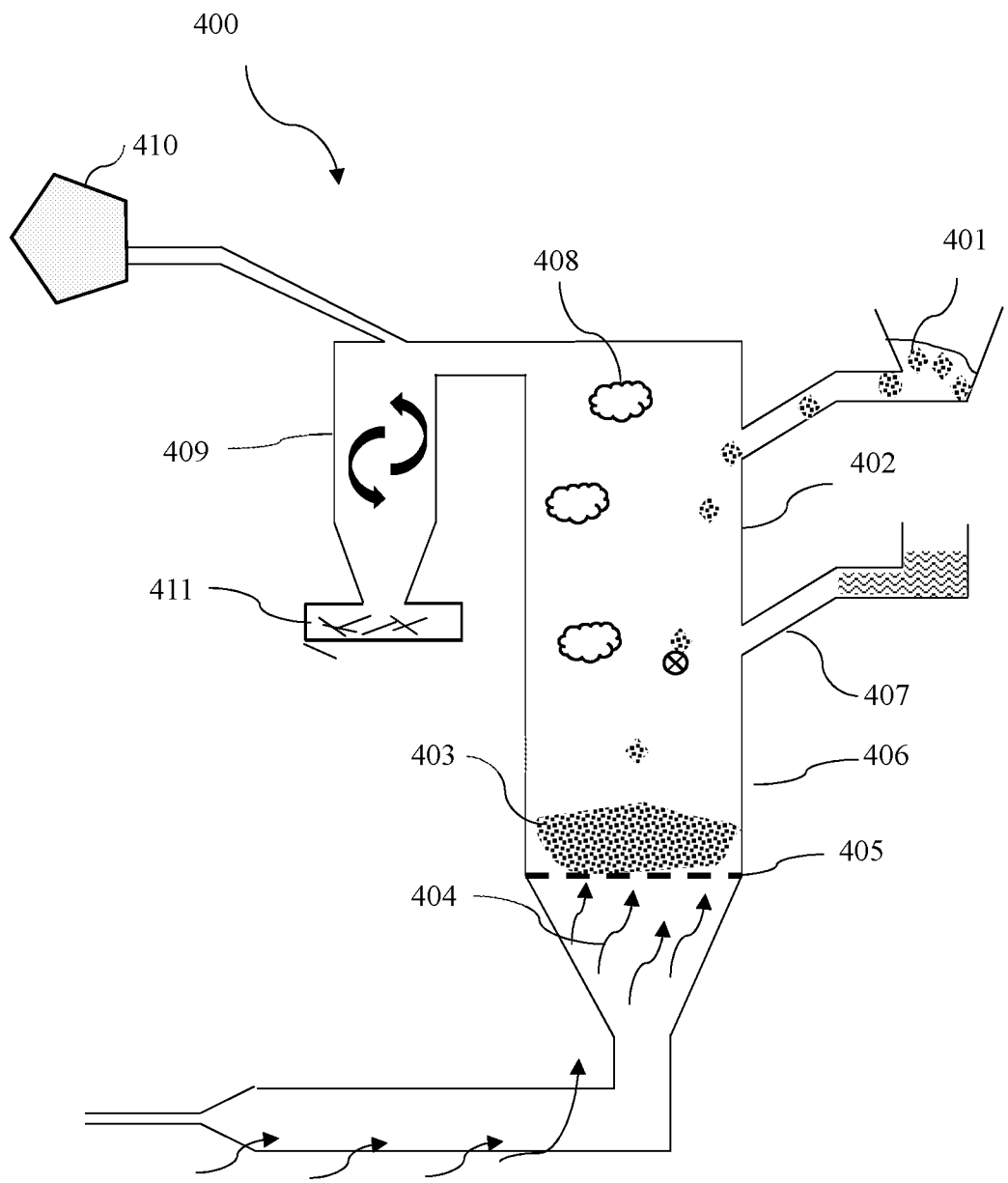

With reference to FIG. 1, the recycling process 100 comprises a step 110 of introducing the article to be recycled into a system suitable for recycling, more particularly into a reactor of said system. Depending on the system used, this reactor may be a portion of a twin-screw extruder 300 as illustrated in FIG. 3, or the reactor 402 of a fluidized-bed device 400 as illustrated in FIG. 4, or a mixer-conveyor not shown in the figures.

In one embodiment, the recycling process also comprises the introduction 120 of a depolymerization-initiating catalyst into the system according to the invention for thermoplastic polymer recycling. The depolymerization-initiating catalyst may be more particularly introduced into a depolymerization reactor or into the hydrolysis reactor, if the depolymerization and hydrolysis are performed in the same reactor. In other words, the depolymerization is performed in the hydrolysis reactor.

In a first preferred embodiment of the invention, the depolymerization step (130) and the hydrolysis take place in the same reactor.

In one variant of the first preferred embodiment of the invention, there is a step of depolymerization alone before the depolymerization step (130) and the hydrolysis which take place in the same reactor.

For example, the depolymerization-initiating catalyst may be an organic peroxide, an inorganic peroxide or superoxide such as barium peroxide ($BaO_2$), potassium superoxide ($KO_2$), cesium superoxide ($CsO_2$), a percarbonate, a peroxyhydrate compound, salts thereof and also a mixture thereof. Depolymerization-initiating catalysts that may be mentioned include hydrogen peroxide ($H_2O_2$), azobisisobutyronitrile (AIBN), sodium (or potassium or magnesium or calcium) carbonate peroxyhydrate ($2Na_2CO_3 \cdot 3H_2O_2$), ammonium carbonate peroxyhydrate (($NH_4)_2CO_3 \cdot H_2O_2$), urea peroxide ($CO(NH_2)_2 \cdot H_2O_2$), sodium sulfate peroxyhydrate ($2Na_2SO_4 \cdot H_2O_2 \cdot 2H_2O$), complexes of $H_2O_2$ and of inorganic salts, the peroxyhydrate of poly(vinylpyrrolidone) polymer ($PVP \cdot H_2O_2$), persulfates, permanganates, perborates, and peroxyhydrates of phosphate salts. Preferably, the depolymerization-initiating catalyst is chosen from perborates or percarbonates. More preferably, the depolymerization-initiating catalyst is sodium percarbonate.

In a preferred embodiment, the depolymerization-initiating catalyst is not liquid at 25° C. In a first preferred embodiment, the depolymerization-initiating catalyst is solid at 25° C. If the depolymerization-initiating catalyst is liquid in pure form at 25° C., it is, in a second preferred embodiment, supported by a solid or impregnated in a solid to form a powder or granules that are solid at 25° C.

The amount of depolymerization-initiating catalyst in the reactor may be such that the mole ratio between the amount of moles of depolymerization-initiating catalyst and the amount of moles of (meth)acrylic thermoplastic polymer present in the article introduced is between 0.001 and 10, preferably between 0.005 and 5, more preferably between 0.01 and 1, and even more preferably between 0.01 and 0.5.

The recycling process according to the invention comprises a step 130 of partial or total depolymerization of the (meth)acrylic thermoplastic polymer resin. This depolymerization may be a conventional depolymerization step and preferably leads to the formation of (meth)acrylate monomers. However, as has been mentioned, the depolymerization may also lead to the formation of impurities, e.g. methyl isobutyrate). As will be detailed hereinbelow, preferably, the depolymerization and hydrolysis reactions take place successively and may proceed in the same reactor or in two different reactors.

The recycling process may thus include a depolymerization step in which the (meth)acrylic thermoplastic polymer resin (e.g. the PMMA resin) is depolymerized via conventional methods leading predominantly to the formation of (meth)acrylate monomer (e.g. methyl methacrylate). The conventional depolymerization methods may be thermal pyrolysis, microwave-induced pyrolysis or fluidized-bed depolymerization, for example. Such a depolymerization may be initiated within the polymer chain, i.e. at any point in the polymer chain, and, in this case, it leads to the formation of two polymers of reduced molecular masses. The depolymerization may also be initiated at one end of the polymer chain and then extend along the chain to lead to the formation of base monomer or base comonomers, and a polymer of reduced chain.

The at least partial depolymerization may be partial depolymerization or total depolymerization.

During the depolymerization, the temperature in the reactor may be between 300° C. and 400° C. or, for example, less than or equal to 350° C. in the presence of a depolymerization catalyst.

Advantageously, the depolymerization may be followed by a purification step during which the (meth)acrylate monomer (e.g. methyl methacrylate) thus obtained may be collected by fractional distillation, for example, to lead to fractions F1 and to fractions F2. The fractions F1 and F2 are different, and F1 may correspond to a pure fraction comprising at least 90% of methyl methacrylate, and F2 may correspond to a less pure fraction in which impurities such as methyl isobutyrate are predominant. The fraction F1 may undergo upgrading as methyl methacrylate, whereas the fraction F2 will undergo a hydrolysis step according to the invention by means of the system according to the invention suitable for thermoplastic recycling. Thus, the process according to the invention may advantageously comprise a distillation step prior to the hydrolysis step.

As mentioned previously, the depolymerization may be separated in time or space from the hydrolysis.

The recycling process according to the invention also comprises a step 140 of introducing a hydrolysis catalyst into a reactor (i.e. a hydrolysis reactor). This hydrolysis catalyst may have acidic, basic or acido-basic properties. The acidic hydrolysis catalyst may be an inorganic acid or an organic acid such as acetic, formic, nitric, benzoic, hydrochloric, sulfuric, orthophosphoric, phosphoric or boric acid, this list not being limiting.

The basic hydrolysis catalyst may be, for example, sodium hydroxide NaOH, potassium hydroxide KOH, sodium carbonate $Na_2CO_3$, $Mg(OH)_2$, $MgCO_3$, $CaCO_3$, a basic zeolite, a hydrotalcite, or ammonia, this list not being limiting.

The hydrolysis catalyst may be a solid heterogeneous catalyst (not liquid under the hydrolysis conditions), for example a metal oxide such as alumina $Al_2O_3$, magnesium oxide MgO, calcium oxide CaO, magnesium hydroxide $Mg(OH)_2$ or calcium hydroxide $Ca(OH)_2$, aluminum hydroxide $Al(OH)_3$, a zeolite, a silicoaluminate, a silica or a mixture thereof. In a preferred embodiment, the catalyst is an alumina-based catalyst. The hydrolysis catalyst is not a resin with acidic groups.

The hydrolysis catalyst is selected from: alumina, MgO, CaO, $Mg(OH)_2$, $Ca(OH)_2$, $Al(OH)_3$, a zeolite, an acid, a base, an amphoteric compound or a mixture of two or more of these compounds.

The hydrolysis catalyst may be mixed, by dissolution or dilution, with water to form an aqueous solution. The aqueous solution containing the dissolved or diluted catalyst can then be introduced (and optionally vaporized beforehand) in the reactor of a system suitable for thermoplastic polymer recycling such as those described previously. The hydrolysis catalyst may also be placed in suspension in water.

The amount of hydrolysis catalyst in the reactor may be between 0.1% and 20% by weight of the (meth)acrylic thermoplastic polymer (e.g. PMMA) present in the article introduced, preferably between 0.5% and 10% by weight and even more preferably between 1% and 5% by weight.

The temperature of the catalyst, when it is an inorganic solid, entering the reactor during step 140 of introduction of a hydrolysis catalyst into a reactor is at least 300° C., preferably at least 350° C., more preferably at least 400° C. and advantageously at least 450° C.

The recycling process according to the invention notably comprises a step 150 in which water, for example in gaseous or liquid form, is introduced into the hydrolysis reactor of the system according to the invention suitable for thermoplastic polymer recycling.

Preferably, in a step 150, a gas comprising steam is introduced into the reactor.

In one variant, step 150 may correspond to the introduction of an aqueous solution into the reactor of the system. By means of the heat generated by a heating means and/or generated by a device suitable for heat recovery, the aqueous solution is transformed into gas comprising steam so as to simultaneously perform the depolymerization and the hydrolysis. Preferably, the hydrolysis is performed after the depolymerization.

Preferably, the amount of water is at least stoichiometric relative to the amount of (meth)acrylate monomers to be hydrolyzed. This means that the molar amount of water is at least 1 mol/l mol relative to the molar amount of (meth)acrylate monomers to be hydrolyzed. More preferably, the amount of water added during step 150 is greater than the amount of (meth)acrylate monomers to be hydrolyzed. For example, in the context of the hydrolysis of a PMMA composed on average of 1000 methyl methacrylate units, the process according to the invention will include a step 150 of introducing water in an amount corresponding to 1000 water units at least so as to hydrolyze everything.

Advantageously, the weight amount of water added is greater than or equal to 15% of the mass of the (meth)acrylic thermoplastic polymer (e.g. PMMA) present in the article introduced, preferably greater than or equal to 20% and more preferably greater than or equal to 40%.

It may also be noted that the amount of water should preferably not be too high so as to limit the energy consumed. Thus, preferably, the weight amount of water added is less than or equal to 100% of the mass of the (meth)acrylic thermoplastic polymer (e.g. PMMA) present in the article introduced.

In a step 160, the (meth)acrylic thermoplastic polymer resin of the article is converted into a mixture comprising (meth)acrylic acid. More particularly, there is conversion, in the hydrolysis reactor, of at least part of the (meth)acrylate monomers into (meth)acrylic acid. This mixture may also comprise, depending on the conditions, a polymer of reduced molecular mass and a monomer in (meth)acrylic ester form.

The hydrolysis reactor is heated to a temperature of between 100° C. and 250° C., preferably between 125° C. and 250° C. and more preferably between 150° C. and 250° C.

During the hydrolysis, the temperature in the reactor may be between 100° C. and 250° C., preferably between 125° C. and 250° C. and more preferably between 150° C. and 250° C., for example 200° C. Preferably, the temperature in the reactor is between 150° C. and 200° C.

Based on the physicochemical properties of the components of this mixture, it is possible to isolate the compounds of interest such as the non-hydrolyzed (meth)acrylic monomers or the (meth)acrylic acids from other undesired compounds. For example, methyl methacrylate and methyl isobutyrate will be clearly separated from the acids by distillation. Next, crystallization may make it possible to separate the butyl esters from the acids, and notably methacrylic acid and acrylic acid from the rest of the compounds.

Table 1 presents the properties of some of the compounds that may be found in the context of the process according to the invention.

TABLE 1

| | | Boiling point | Melting point |
|---|---|---|---|
| n-Butyl methacrylate | | 162-165° C. | −75° C. |
| Methacrylic acid | | 163° C. | 16° C. |
| Isobutyric acid | | 155° C. | −47° C. |
| Butyl acrylate | | 145° C. | −64° C. |
| Acrylic acid | | 141° C. | 14° C. |
| Methyl methacrylate | | 101° C. | −48° C. |
| Methyl isobutyrate | | 90° C. | −85° C. |

Via step 160, the process according to the invention makes it possible to obtain a composition notably comprising a mixture of (meth)acrylic acids. As a function of the composition of the (meth)acrylic thermoplastic polymer resin of the article, this mixture may contain, besides methacrylic acid and acrylic acid, a wide diversity of compounds. Specifically, the (meth)acrylic thermoplastic polymers may be depolymerized into monomers and the monomers are then optionally partially hydrolyzed to give the corresponding acids. For example, the mixture may comprise butyl and ethyl esters such as n-butyl methacrylate, methyl methacrylate, methacrylic acid, isobutyric acid, butyl acrylate, ethyl acrylate, methyl acrylate and acrylic acid.

In this context, the recycling process according to the invention may show high efficiency during its coupling with distillation and/or crystallization steps since, as a result of the differences in boiling point and/or melting/crystallization point between the compounds of interest and the impurities, it is possible to obtain relatively pure compositions of upgradable compounds.

The purification may lead to the formation of several more or less pure fractions. For example, methyl methacrylate may be recovered to be upgraded as such or is reintroduced into the hydrolysis reactor, in order to be hydrolyzed. It is then possible to perform a virtually complete depolymerization of the (meth)acrylic polymer and to improve the yields of methacrylic acid, for example, by means of this reactor refeeding system while at the same time reducing the energy cost of the system.

Thus, the process according to the invention advantageously comprises one or more purification steps 170.

The process may include a step 171 of distillation of the (meth)acrylic acids and of the (meth)acrylic esters present following the introduction of steam. This separation step allows separation due to the differences in boiling point of the various compounds present. Advantageously, this step may make it possible to generate a mixture predominantly including methyl methacrylate and/or methyl isobutyrate. Preferably, this step may make it possible to generate a mixture predominantly including methyl methacrylate.

The (meth)acrylic esters recovered after distillation may be reinjected into the hydrolysis reactor in order to be placed in contact with steam. This makes it possible to hydrolyze the monomers to give the corresponding acids. For example, the monomer produced during the implementation of the recycling process may be condensed and collected by distillation in a container intended for this purpose, and the collected monomer may then be reinjected into the reactor via a return means connected to the reactor and to the collector. It is then possible to perform a virtually complete depolymerization of the (meth)acrylic polymer and to improve the yields of methacrylic acid, by means of this reactor refeeding system. Thus, advantageously, the process according to the invention includes a step of reinjecting into the hydrolysis reactor a fraction formed during the distillation step. This fraction preferably includes a majority of compounds bearing an ester function.

Thus, in one variant, the recycling process comprises a step in which an ester (e.g. a (meth)acrylate monomer) produced in the system is separated by distillation 171, and the ester is then reintroduced into the hydrolysis reactor of the system suitable for thermoplastic recycling, in order to be hydrolyzed.

The process according to the invention, and more particularly after a distillation step, makes it possible to obtain a mixture predominantly including n-butyl methacrylate, methacrylic acid, isobutyric acid, butyl acrylate and/or acrylic acid. Preferably, this step may make it possible to generate a mixture predominantly including methacrylic acid and/or acrylic acid. The mixture predominantly including methacrylic acid may notably be contaminated with isobutyric acid. On account of the differences in melting point between these compounds, it is possible to separate methacrylic acid and isobutyric acid by crystallization in molten medium. Thus, advantageously, the process may include a crystallization step 175. Advantageously, this step may make it possible to generate a mixture enriched in methacrylic acid and more particularly a composition predominantly including methacrylic acid.

More preferably, this step may make it possible to generate a mixture predominantly including methacrylic acid. For example, the hydrolysis of PMMA (following a depolymerization step) may lead to methacrylic acid and to contaminants such as isobutyric acid. By means of the difference in melting point/crystallization temperature (see table 1) between methacrylic acid and isobutyric acid, it is possible to perform a purification by crystallization in molten medium of the methacrylic acid. This purification method is simple and inexpensive to perform. Specifically, at 25° C., all the acids are liquid; by reducing the temperature to 0° C., for example, the acrylic and methacrylic acids solidify, in contrast with isobutyric acid. Purging the reactor makes it possible to remove the isobutyric acid. Several crystallizations may be performed in cascade so as to improve the purity.

Advantageously, the recycling process according to the invention may also comprise a step 180 of regenerating the catalyst and more particularly of the hydrolysis catalyst.

For example, when the hydrolysis catalyst is a heterogeneous catalyst, the process may also comprise a step consisting in placing said hydrolysis catalyst in contact with a regenerative substance so as to reactivate said hydrolysis catalyst. In the case where the catalyst is contaminated, its regeneration may be performed with a stream of air at at least 400° C. or alternatively with depleted air for better temperature control or else under a stream of hydrogen. According to another variant, the regeneration is performed using a stream of ozone in the case of deposition of carbon. Finally, in the case where the catalyst is deactivated by metallic contaminants, simple scrubbing or, as a last resort, replacement thereof may be performed.

In addition, when the article to be recycled is a composite article based on (meth)acrylic thermoplastic polymer resin, the recycling process according to the invention may advantageously also comprise a heat recovery step 190.

In this case, the article to be recycled made of polymer composite material including a reinforcer is introduced into a reactor of the recycling system 200 (e.g. a depolymerization reactor). The introduction of the article may be accompanied by a step of introducing a depolymerization-initiating catalyst as described previously and optionally by adding water. Preferably, the depolymerization reactor of the recycling system does not comprise any water.

The temperature in the reactor allows energy input in the form of heat which promotes the depolymerization of the thermoplastic polymer resin into a mixture of products such as polymers of reduced molecular mass and one or more monomers in (meth)acrylic ester form. In addition, during the depolymerization, the reinforcer stores heat and this heat may advantageously be used in the recycling system. Specifically, the heat contained in the reinforcer may be transferred by means of a heat exchanger. The energy stored by the heat exchanger may be used, for example for heating the water used in the context of the conversion step 160. The heat contained in the reinforcer may be transferred to the water which transforms into steam, which can then be transferred into a hydrolysis reactor. The use of heat recovered by means of the heat exchanger makes it possible to dispense with an additional step consisting in heating the water. The re-use of heat makes it possible to reduce the energy cost of such a recycling system.

After transferring energy from the reinforcer to the water, the reinforcer may be recovered via recovery means at the outlet of the heat exchanger and may be reused.

In one embodiment, the process also comprises a step of milling the article to be recycled, the article being milled before it is introduced into the system suitable for polymer recycling. The milling step makes it possible to reduce the dimensions of the article to be recycled and may be performed using a mill and/or a crusher. The article is reduced to dimensions permitting the introduction of the milled material obtained into a system suitable for recycling according to the invention. Thus, the article may be in the form of chips, granules or powder. The article may be introduced into the system suitable for recycling in one form or in several forms. Advantageously, the milling step makes it possible to facilitate the feeding of the reactor of the system suitable for thermoplastic recycling.

In an optional step, the recycling process may comprise a step of line filtration using an endless screw. During this line filtration step, the article is entrained by an endless screw inside a reactor enabling a temperature rise sufficient to fluidize and/or melt at least part of the (meth)acrylic thermoplastic resin. This step then also includes collection of the liquid and viscous resin. Thus, the article, preferably a polymer composite article, is freed of part of the (meth) acrylic thermoplastic resin or freed of the fibers in the case of a fibrous reinforcer, for example, before depolymerization. One object is to send fewer fibers into the reactor.

According to another aspect, the invention relates to a system 200 suitable for (meth)acrylic thermoplastic polymer recycling, more particularly to the recycling of articles based on (meth)acrylic thermoplastic polymer resin. As presented in FIG. 2, the system may advantageously comprise:
- a means 211 for introducing the article into said system 200,
- a hydrolysis reactor 210,
- a means 240 for introducing a hydrolysis catalyst into said hydrolysis reactor,
- a means 250 for introducing water, in liquid or gaseous form, into said hydrolysis reactor, and
- a heating means 260, which is preferably suitable for inducing the depolymerization and hydrolysis of at least a part of the article to be recycled.

A system suitable for the recycling of an article based on (meth)acrylic thermoplastic polymer resin may be, for example, a "reactive" extruder/conveyor (with external heating). A reactive extruder performs both a mechanical treatment of the article and a treatment which induces chemical changes in the constituent polymer. The use of an extruder for performing the recycling process is advantageous from the environmental, security and safety viewpoint of the process. Specifically, an extruder makes it possible to process molten polymers of high viscosity without the need to add solvent to reduce the viscosity of the molten polymers. The extruder has the advantage of allowing efficient heat transfer from the barrel to the polymer. It also allows temperature control by zone and permits an output of solid (depolymerization residue) and of gas (monomer).

The means 211 for introducing the article into the reactor 210 may be selected, for example, from: an endless screw, a metering device, pneumatic transfer equipment, a gravitational metering device, a rolling belt or a conveyor belt, a hydraulic thruster system. Preferably, the reactor 210 suitable for receiving the article to be recycled is selected from: an endless screw, a conveyor belt and a pneumatic transfer device. For example, the introduction takes place via a feed hopper and an endless screw.

The means 240 for introducing a hydrolysis catalyst into the hydrolysis reactor may be selected, for example, from: a pump, an endless screw, a pneumatic transport device, a conveyor belt. Preferably, the means 240 for introducing a hydrolysis catalyst into the hydrolysis reactor is selected from: an endless screw and a pneumatic transport device.

The means 250 for introducing water into the hydrolysis reactor may be selected, for example, from: a pump, an evaporator, a superheated steam injector. Preferably, the means 250 for introducing water into the said hydrolysis reactor is selected from: a steam injector and a liquid water pump.

The heating means 260 may be selected, for example, from: a tubular or plate exchanger, a microwave oven, a screw extruder/conveyor. Preferably, the heating means 260 is selected from: tubular or plate heat exchangers.

The heating means may advantageously correspond to a pipe suitable for introducing into the hydrolysis reactor steam at a temperature of at least 150° C.

The heating means is preferably suitable for inducing the hydrolysis of at least a part of the article to be recycled. That is to say that it is suitable for heating to a temperature of between 150° C. and 250° C. for a period of at least 20 minutes. Preferably, the heating means is suitable for heating to a temperature of between 175° C. and 250° C. for a period of at least 30 minutes.

In order to enable the recovery of gases originating from the implementation of the recycling process, the system 200 suitable for recycling may comprise one or more purification devices 270. For example, the system may comprise a cooling device which may correspond to a system for separation by distillation, for example a distillation column. The distillation column allows the separation of compounds as a function of their boiling point. By means of the distillation system of the recycling system 200, it is notably possible to separate the (meth)acrylic monomer from its hydrolysis product. It is also possible to recover and recycle the hydrolysis catalyst, in the case where the catalyst is in liquid form.

Figure 2:
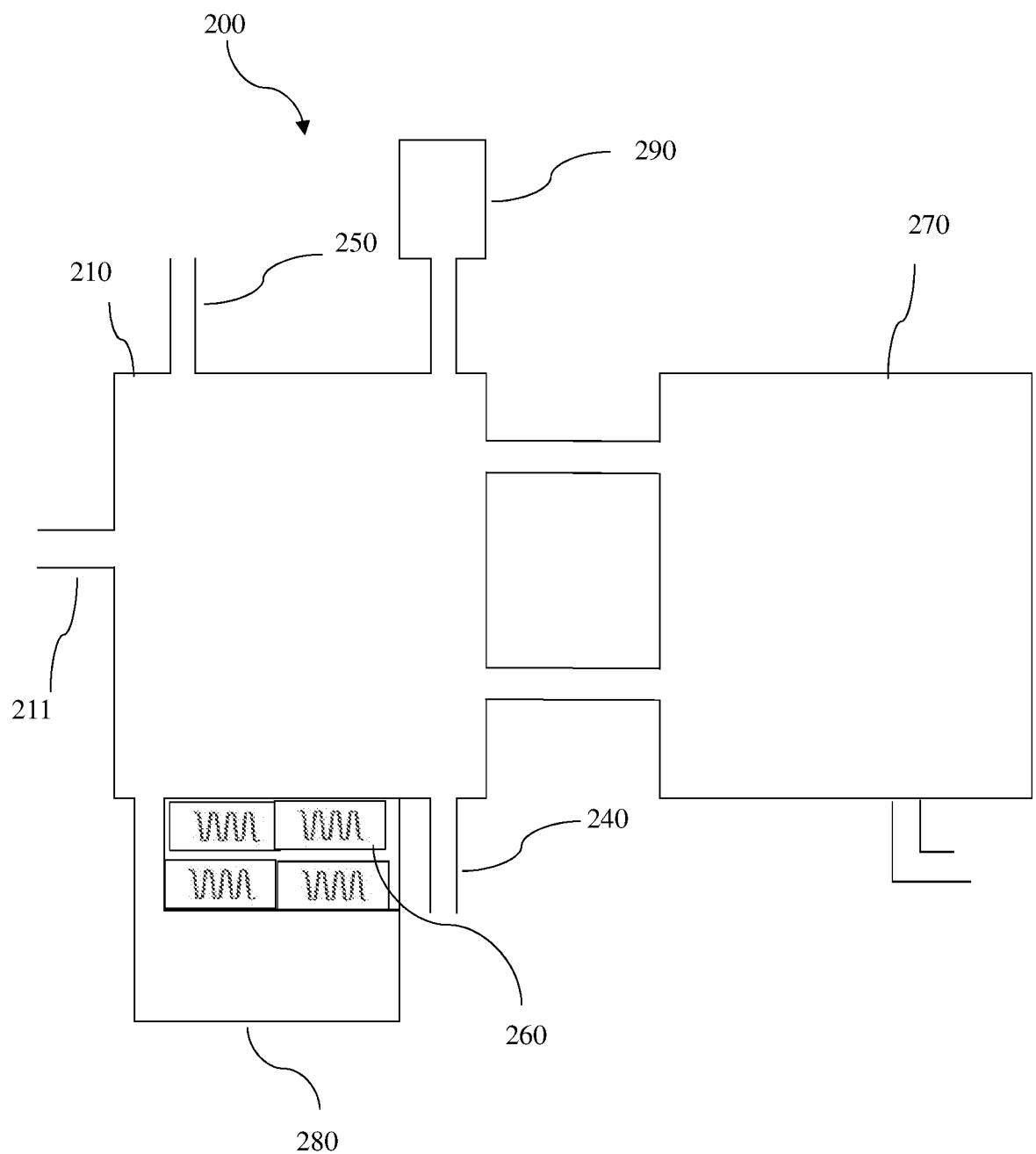

As presented in FIG. 2, in one embodiment variant, the recycling system 200 also comprises a device 280 suitable for heat recovery. Such a heat recovery device 280 may be any device known to those skilled in the art. Such a device makes it possible to recover the heat energy produced during the processes of gas condensation, of cooling of the reactor of the recycling system, or of recovering the heat stored by the reinforcer of an article made of composite material to be recycled. Advantageously, this recovered energy may then be used to produce steam, to heat the reactor or to maintain the pipes at a given temperature. Thus, the device suitable for heat recovery is capable of using the recovered heat to heat water and/or to maintain at least a part of the system according to the invention at a temperature above 100° C.

Such a heat recovery device may be, for example, a heat exchanger. Conventionally, a heat exchanger enables heat transfer between two fluids. In the recycling process, the heat transfer takes place between a solid and a heat-transfer fluid. The solid and the fluid may be fixed, or they may both be in motion, or the solid is fixed while the fluid is in motion. The solid and the fluid may circulate parallel to each other and in the same direction. However, the solid and the fluid may circulate parallel to each other but in opposite directions. They may also circulate perpendicularly.

The heat transfer may be performed by a direct-contact heat exchanger. Thus, during heat transfer performed by a direct-contact heat exchanger, the hot reinforcer is in intimate contact with the heat-transfer fluid. The fluid may be a liquid, for example water, a solvent or a mixture thereof. In other examples, the fluid may be a gaseous fluid such as a stream of air or of gas, for example. The contact with the fluid may be performed using an immersion or spraying device. The contact may also be performed by means of a nozzle or a series of nozzles having holes through which the fluid can escape, the nozzles being oriented toward the solid element. Other heat-transfer fluids may be used; preferably, the fluids available on site are used, for example, water, air, gas, but also the depolymerization coproducts, notably hydrocarbons which may be used as fuel or as secondary heat-transfer fluid. Specifically, the hydrocarbons vaporize, in a similar manner to water, on contact with the hot residue. The hot gas is directed toward a boiler where the hydrocarbons are condensed while bringing the water to the boil. This water will be used in the process or for heating a primary heat-transfer fluid.

As a variant, the heat transfer may be performed by an indirect-contact heat exchanger. Such a heat exchanger may be, for example, a tubular exchanger, a plate exchanger, an exchanger with horizontal tubular bundles, an exchanger with vertical tubular bundles, a helical-coil exchanger, a fin tube exchanger or a rotary or block exchanger. These examples are not limiting, and a person skilled in the art will appreciate that other types of indirect-contact heat exchangers may be used. An indirect-contact heat exchanger may also use a heat-transfer fluid. The heat-transfer fluid may be a liquid, for example water, a solvent or a mixture thereof, molten salts or synthetic oil. For example, such a synthetic oil may be the product sold by the company Arkema under the name Jaryherm®.

The advantage of an indirect-contact heat exchanger is that it enables heat recovery at different thermal levels. In other words, it is possible to recover heat at several thermal levels, each thermal level being associated with a different temperature. It is possible to have heat exchangers in cascade (or in stages) so as to enable heat exchange with the reinforcer which is increasingly less hot from one exchange to the next.

The presence of the hydrolysis catalyst makes it possible to improve the yields of (meth)acrylic acid, but also to lower the reaction temperature. However, the hydrolysis catalyst may be contaminated with the products derived from the depolymerization and/or hydrolysis reaction. Thus, the recycling system may comprise a device 290 for regenerating the hydrolysis catalyst. Such a device makes it possible to reduce the cost of the recycling performed by the system, but also to reduce the production of waste.

In addition, the system according to the invention may include:
a system enabling the withdrawal of solid to remove solid elements from the reactor(s),
sensors for measuring the temperature in the reactor(s),
sensors for measuring the pressure in the reactor(s),
systems enabling the input or output of fluid in the reactor(s), the fluid possibly being in liquid or gaseous form, and/or
pipes for circulating fluids between the various elements of the system.

Figure 5:
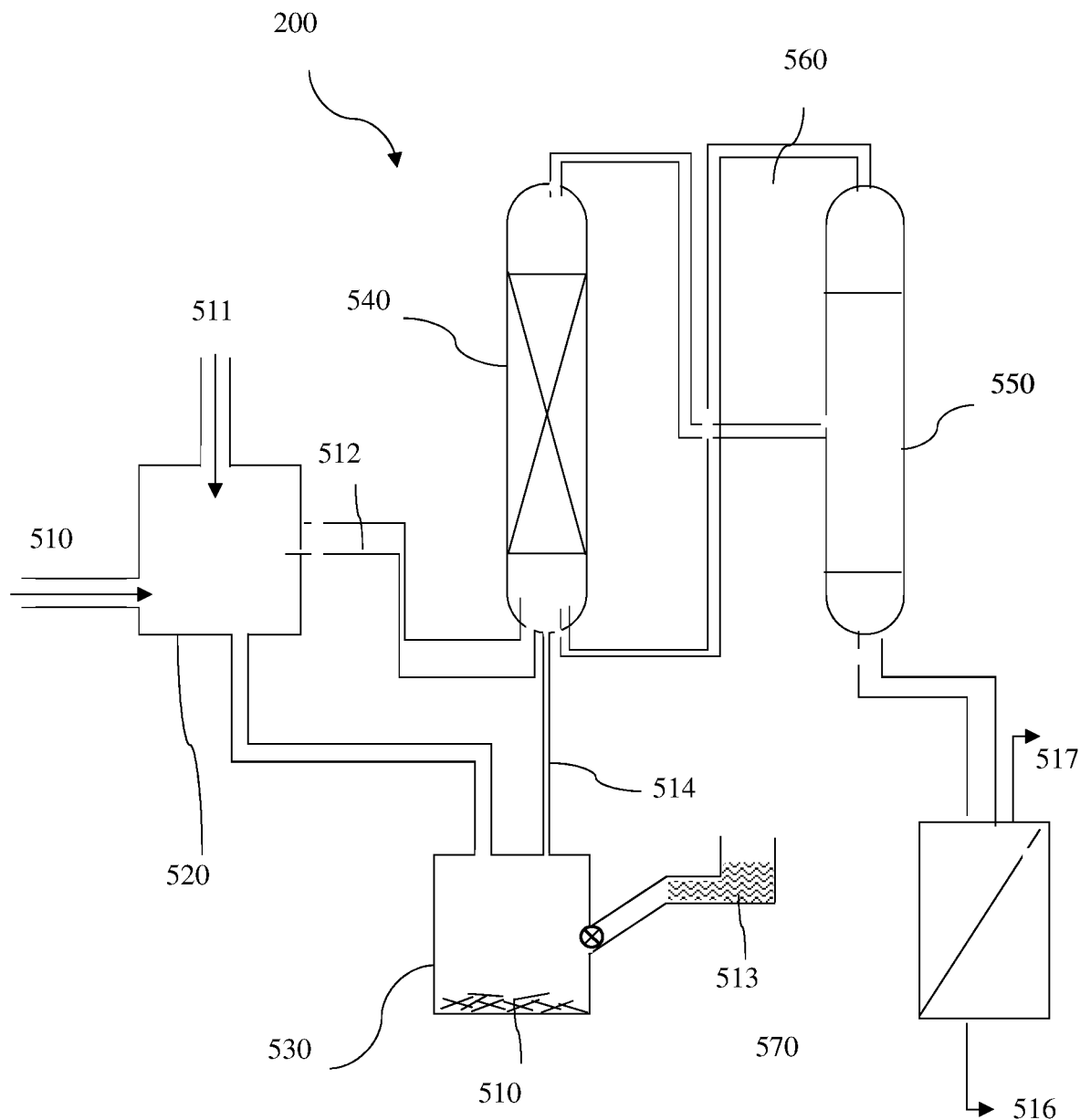

FIGS. 3 to 5 illustrate various embodiments of the system 200 according to the invention.

With reference to FIG. 3, the recycling system according to the invention includes an extruder, more particularly a twin-screw extruder 300 comprising an orifice 301 via which an article 302 comprising a PMMA resin is inserted, for example by means of a metering device 303. The article to be recycled may be in powder or granule form. Alternatively, the article may be introduced into the extruder after having undergone a first depolymerization step.

A twin-screw extruder may be, for example, a Clextral® type extruder. The twin-screw extruder comprises two screws 304, which are usually parallel, rotating inside a barrel 305. Advantageously, the extruder is of modulable nature, i.e. the screw and the barrel are modules assembled in series, and the assembly of which may be modified. In the extruder, the article based on PMMA resin is heated and the resin is rendered molten by means of an external heating means 306 which regulates the temperature of the barrel 305. The temperature in the reactor may be between 50° C. and 550° C. and it may be controlled by means of temperature sensors not shown in the figure. Gas 307 comprising steam, or an aqueous solution 307, is introduced into the extruder 300 to enable the hydrolysis. The depolymerization may lead to products in the form of gases which are extracted from the extruder in order to be processed. The gases produced may be directed via a pipe 308 toward a cooling system 309 in order to be condensed. The condensate obtained may then be collected in a chamber 310 intended for this purpose.

In a second embodiment, the system suitable for recycling an article based on (meth)acrylic thermoplastic polymer resin may include a fluidized-bed device, as illustrated in FIG. 4. Such a circulating fluidized-bed device allows a homogeneous temperature to be obtained within the bed by virtue of a greater area of exchange between the fluid, the particles and the steam, allowing very high heat transfer.

With reference to FIG. 4, the article 401 comprising a composite based on PMMA resin is introduced into a reactor 402 of a fluidized-bed device 400. In this reactor, a mixture of solid particles 403 is suspended in a hot ascending gaseous stream 404, above a support 405, for example a grate. The grate is such that it does not allow particles to pass but allows gases to pass. The mixture of solid particles comprises an inert fluidization medium, for example sand, and comprises the premilled article 401 to be recycled. The ascending gaseous stream is a stream of fluidization gas, for example air and/or vapor of an aqueous solution. Preferably, the gas contains less than 10% by weight of dioxygen. The fluidization gas is injected into the bottom part 406 of the reactor and its flow rate is such that it must enable fluidization of the mixture of particles. The gas flow drives movement of the mixture of particles and blending promoting the heat transfer. The reactor may also comprise means 407 for feeding in water to enable the introduction either of steam or of an aqueous solution. In the case where the water is in the form of an aqueous solution, this solution is vaporized in situ in the reactor. In addition, these feed means 407 may comprise a means for introducing the hydrolysis catalyst. In the reactor, the PMMA resin is depolymerized by the action of heat to lead notably to the methyl methacrylate monomer. Said monomer is hydrolyzed to methacrylic acid in the reactor by means of steam. The methyl methacrylate monomer and the methacrylic acid are in gaseous form 408 and are entrained out of the reactor toward a gas/solid separator 409 such as a cyclone. Using a cooling system 410, the gases may be condensed in a chamber intended for this purpose. The gas/solid separator enables the recovery of the solids, for example the reinforcer 411 derived from a composite. Such a reinforcer generally refers to mineral fillers or to a plurality of fibers, unidirectional rovings or a continuous filament mat, fabrics, felts or nonwovens which may be in the form of strips, webs, braids, strands or parts.

According to one variant, the fluidized-bed device for the recycling of an article based on (meth)acrylic thermoplastic polymer resin may be a circulating fluidized-bed device. Such a circulating fluidized-bed device has a greater fluidization speed than in a conventional fluidized-bed device. This speed is of the order of 4 to 8 m/s. In this type of fluidized bed, the upper limit of the bed is not sharp and the entrainment of the particles above the bed is greater. This device has the advantage of enabling better heat exchange between the solid particles.

In a third embodiment, the system suitable for the recycling of an article based on (meth)acrylic thermoplastic polymer resin includes a device of mixer-conveyor type, for example a paddle dryer mixer-conveyor. This device comprises a reactor in which is placed a coil. The coil thus enables the mixing and homogenization of a mixture comprising the article to be recycled and steam. The mixer-conveyor has the advantage of enabling large amounts of solid waste/residues to be processed. It also enables good heat transfer between the wall and the waste. Such a device may be used at low temperature for drying a solid, but, in the context of the invention, by increasing the temperature, it is possible to induce hydrolysis and possibly preliminary depolymerization.

Another type of system suitable for the recycling of an article based on (meth)acrylic thermoplastic polymer resin includes a device consisting of hollow plates heated by a heat-transfer fluid circuit (steam under pressure, oil, molten salts, etc.). In the course of its treatment, the article advances over the plates of increasing temperatures in a first stage. The solid residue ends its passage through the reactor by passing over plates which are at a lower temperature and where the heat exchange takes place from the residue to the heat-transfer fluid. The heat-transfer fluid thus heated can then serve to preheat the article toward the reactor inlet.

FIG. 5 illustrates, according to one embodiment of the invention, a recycling system coupled to a device 530 suitable for heat recovery.

The depolymerization reactor 520 of the recycling system is suitable for receiving an article 510 to be recycled made of polymer composite material including a reinforcer and an initiating catalyst 511. Advantageously, the depolymerization reactor 520 of the recycling system does not comprise any water.

In addition, the depolymerization reactor includes a pipe 512 suitable for transferring at least a portion of the mixture formed during the depolymerization and a heat recovery device 530 suitable for receiving the reinforcer 510 which has stored heat during the depolymerization step.

As presented in FIG. 5, the device 530 suitable for heat recovery may be coupled to a water tank 513 and to a pipe 514 and is configured to transfer the heat contained in the reinforcer to the water, which transforms into steam and is then transferred to the hydrolysis reactor 540 via the pipe 514. Thus, the heat-recovery device 530 makes it possible to reduce the energy cost of such a recycling system.

In addition, the device 530 suitable for heat recovery may comprise means for recovering the reinforcer which will be able to be upgraded.

As mentioned previously, the system 200 according to the invention includes a hydrolysis reactor 540 suitable for hydrolyzing the esters. For example, methyl methacrylate will be hydrolyzed to methacrylic acid and methyl isobutyrate will be hydrolyzed to isobutyric acid.

The system also includes a fractional distillation device 550 for separating the acids from the other impurities (e.g. esters). In addition, the fractional distillation device 550 enables the reinjection of the esters into the hydrolysis reactor 540, via a pipe 560, and the transfer of the acids into a crystallization device 570.

The crystallization device 570 is capable of separating the impurities such as the isobutyric acid 517 from the methacrylic acid 516.

Figure 6:
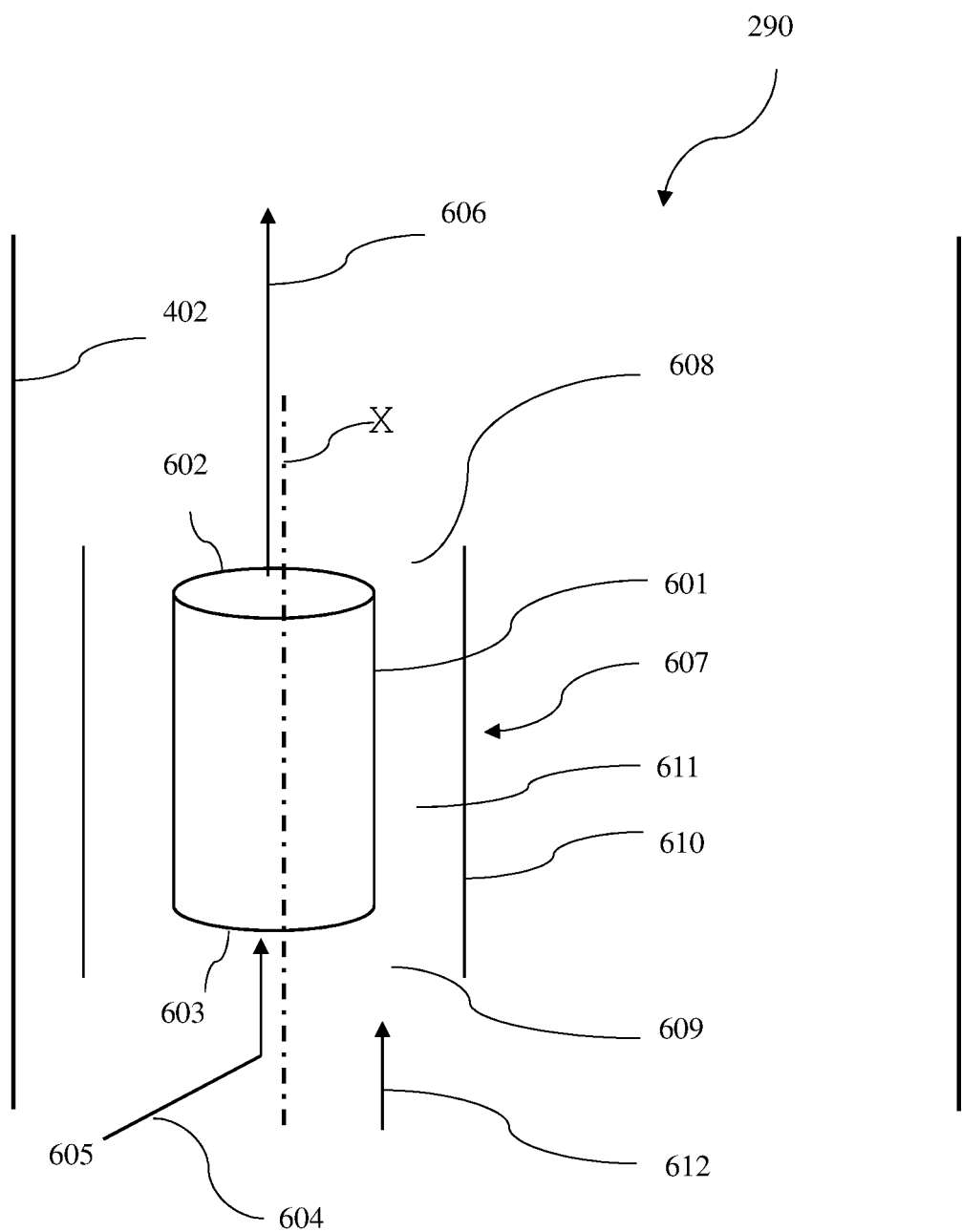
Figure 7A:
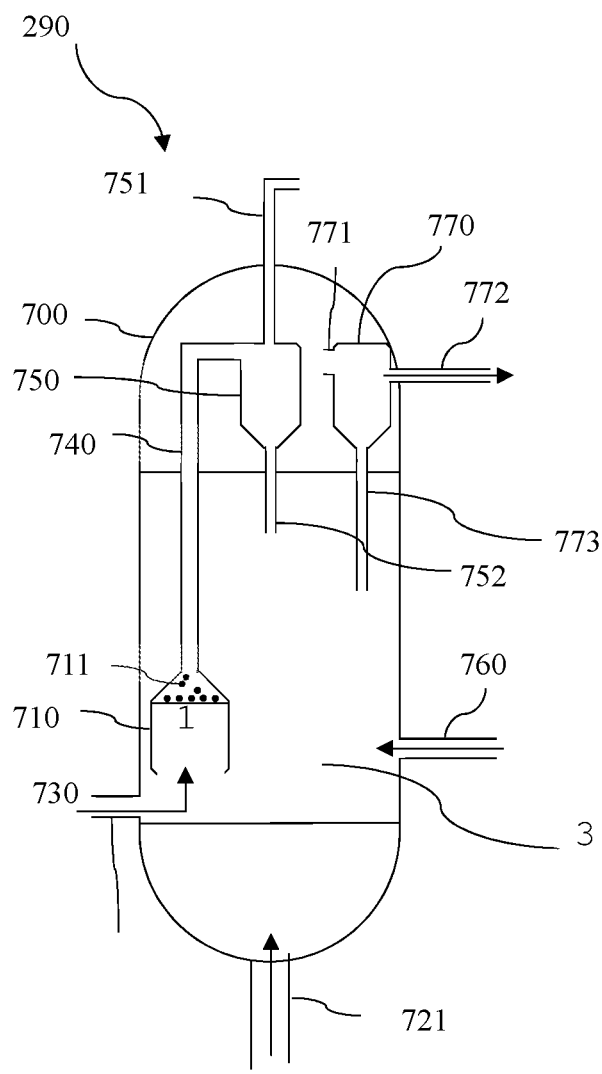
Figure 7B:
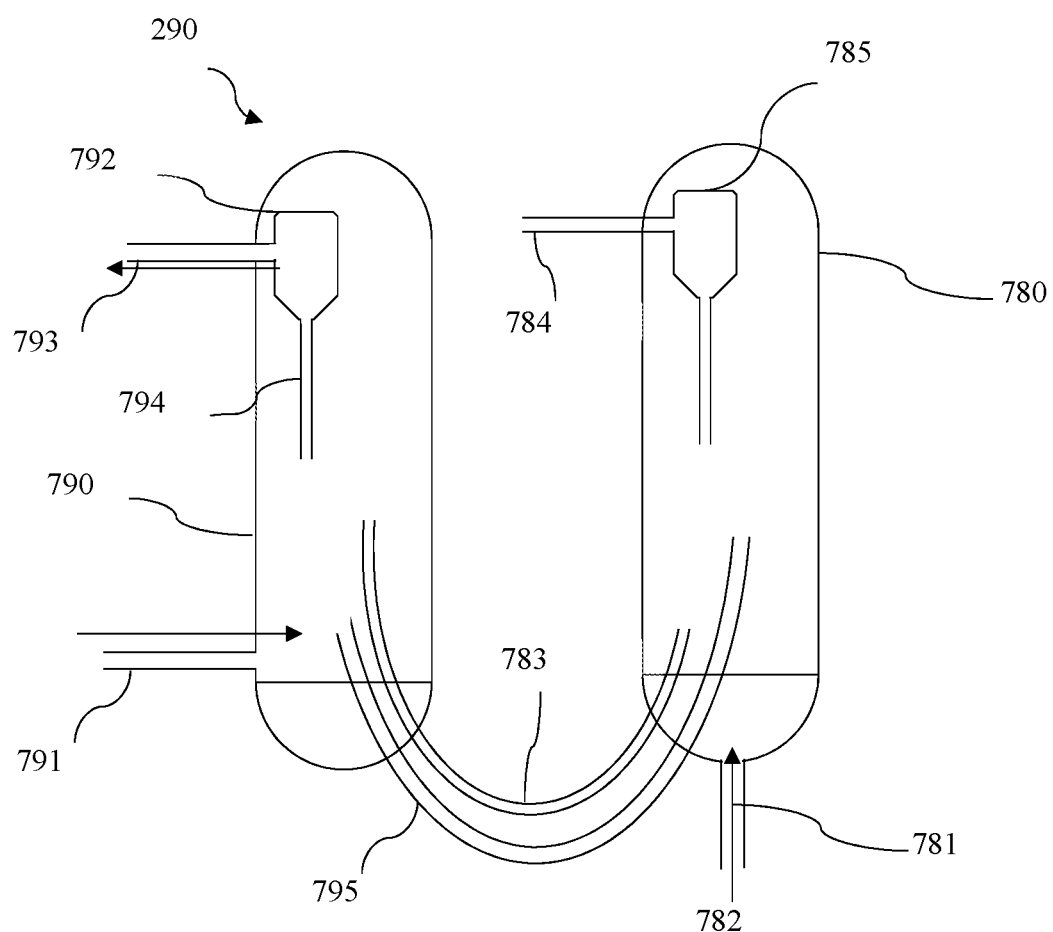
Figure 8:
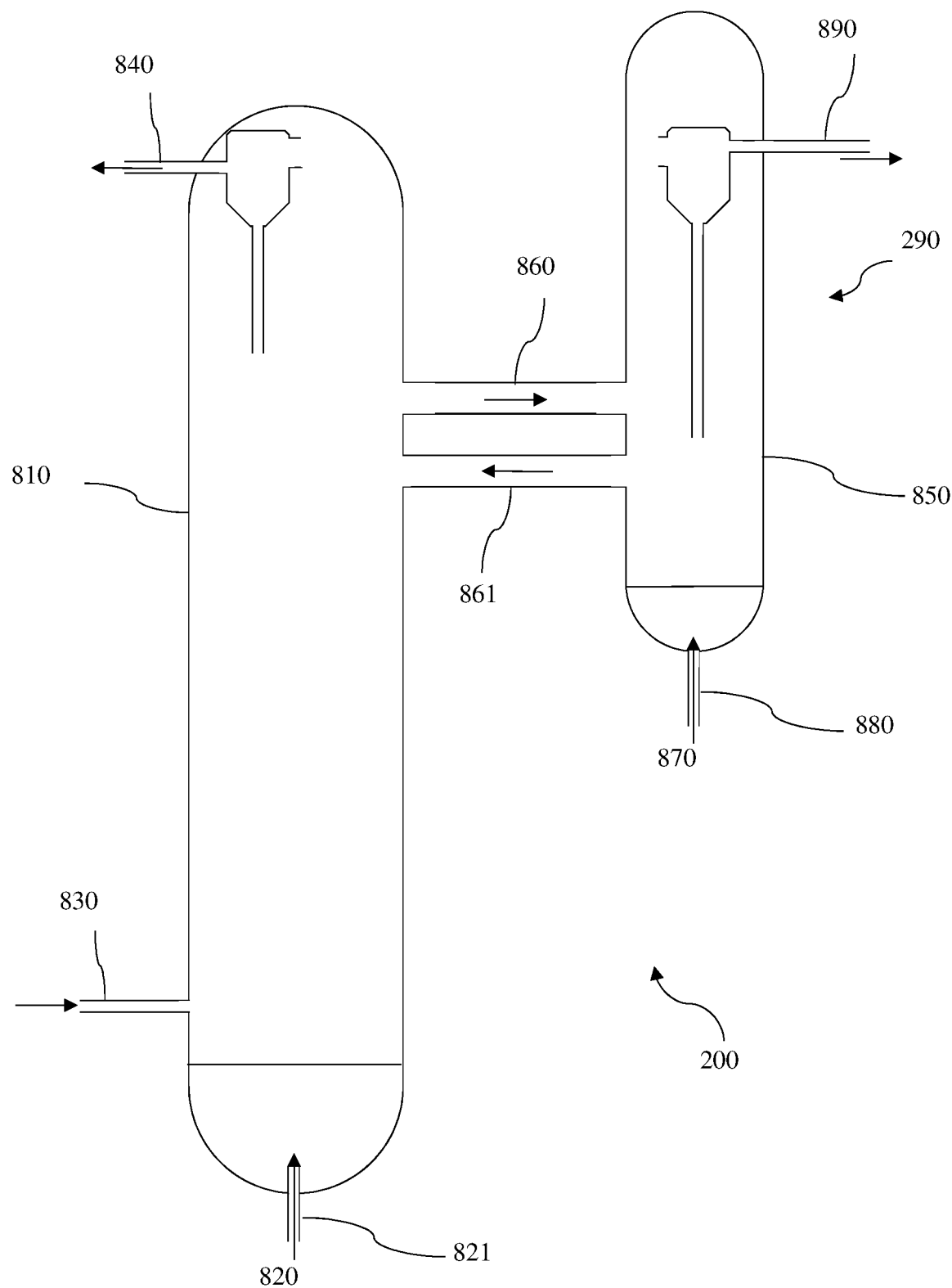

FIGS. 6 to 8 illustrate various embodiments of a hydrolysis catalyst regenerating device 290.

With reference to FIG. 6, the regenerating device 290 may be placed inside the reactor 402 of a fluidized-bed recycling system 400. The regenerating device may comprise a chamber 601 having a main axis X, a distal end 602 and a proximal end 603. The chamber is connected to a feed pipe 604 located at the proximal end 603 for feeding the chamber of the regenerating device with regenerative substance 605.

In the case where the catalyst is contaminated, its regeneration may be performed with a stream of air at at least 400° C. or alternatively with depleted air for better temperature control or else under a stream of hydrogen. According to another variant, the regeneration is performed using a stream of ozone in the case of deposition of carbon. Finally, in the case where the catalyst is deactivated by metallic contaminants, simple scrubbing or, as a last resort, replacement thereof may be performed.

The chamber 601 of the regenerating device is also equipped with a pipe 606 permitting the output of fluid or of particles from the chamber. An element 607 is placed around the chamber 601. The element 607 is open at these two ends 608 and 609, and has a wall 610 radially surrounding the chamber 601 relative to the axis X. The element 607 is arranged so as to create a zone 611 in which the speed of the hydrolysis catalyst particles is reduced relative to that of the same fluidized particles in the reactor 402. Counter-pressure injection means 612 are provided at the proximal end 603 to enable the introduction of the hydrolysis catalyst into the regenerating device. Once regenerated by means of the regenerator 603, the hydrolysis catalyst is transported toward the pipe 606, for example by pneumatic transport, to be reinjected into the reactor 402.

A hydrolysis catalyst regenerating device 290 according to another embodiment is illustrated in FIG. 7A. In this embodiment, the hydrolysis catalyst regenerating device 290 is located inside the hydrolysis reactor 700. The hydrolysis catalyst regenerating device 290 may comprise:

A chamber 710 suitable for receiving the hydrolysis catalyst particles and also a regenerative substance in order to reactivate the hydrolysis catalyst, Means 720 for feeding the chamber with the regenerative substance, Means for introducing the hydrolysis catalyst into the regenerating chamber, and Means 752 for introducing the reactivated hydrolysis catalyst into the reactor of the recycling device.

According to this embodiment, the recycling system preferably functions as a fluid bed as described previously and comprises a regeneration zone 1 and a reaction zone 2. The regeneration zone and the reaction zone are separated by separating means 711 such as a separating wall which may be tubular or of circular cross section. Preferably, the reaction zone 2 is located outside the separating means and the regeneration zone 1 is located inside the separating means. In addition, the regeneration zone and the reaction zone communicate via the separating means for the circulation of the catalyst from the reaction zone to the regeneration zone. The catalyst may be present in the reaction zone in the form of a fluidized bed 3 or integrated into the fluidized bed 3.

The recycling system is fed with fluidization gas via the injection means 721. The fluidization gas is a gas whose flow rate is suitable for enabling the fluidized bed to be in fluidized form. Advantageously, the fluidization gas comprises steam. Preferably, these injection means are located under the hydrolysis reactor to promote homogeneous feeding with fluidization gas. Moreover, the reaction zone is fed with reaction fluid comprising the (meth)acrylate monomer, for example derived from the depolymerization, by feed means 760.

The internal regenerator 710 for regenerating the catalyst comprises means 720 for feeding the internal regenerator 710 with regenerative substance 730. The internal regenerator enables the regenerative substance 730 to be placed in contact with the hydrolysis catalyst. The regeneration may be performed with a stream of air at at least 400° C. or alternatively with depleted air for better temperature control or else under a stream of hydrogen or a stream of ozone. The flow rate of the regeneration stream is adapted such that the fluidized bed in the regeneration zone is a rapid fluidized bed; the linear speed of the gas therein is preferably higher than in the reaction zone. The regeneration of the catalyst takes place predominantly in the regeneration zone, but the regeneration is not total and the catalyst is transported by pneumatic transport via a pipe 740 located in the top part of the internal regenerator to a first separator 750, for example of cyclone type. The separator comprises a first evacuation pipe 751 for removing the gases generated during the reactivation of the hydrolysis catalyst such as $O_2$, $CO_2$, $N_2$, CO and a second pipe 752 for injecting the catalyst into the reaction zone.

The reactivated catalyst is then inside the reaction zone and in the presence of (meth)acrylate monomer derived from the depolymerization 760, which makes it possible to give (meth)acrylic acid.

A second separator 770, for example of cyclone type, is located in the top part of the reactor. The second separator comprises an aperture 771, an evacuation pipe 772 for recovering the reaction products, notably the (meth)acrylic acid at the outlet of the recycling device. The second separator comprises a reinjection pipe 773 for reinjecting the catalyst into the reaction zone. Thus, by means of such a device for regenerating the hydrolysis catalyst inside the recycling system, the (meth)acrylic acid yields are improved, the hydrolysis of the (meth)acrylate monomer is virtually complete and the regeneration of the hydrolysis catalyst makes it possible to reduce the costs of such a system and improves the environmental impact.

In one embodiment variant, the regenerating device 290 may be located outside the hydrolysis reactor. In particular, another embodiment of recycling of the hydrolysis catalyst is illustrated in FIG. 7B. In this embodiment, the hydrolysis catalyst regenerating device 780 is located outside the hydrolysis reactor 790.

The hydrolysis catalyst regenerator 780 comprises means 781 for feeding the regenerator with regenerative substance 782. The regenerator enables the regenerative substance 782 to be placed in contact with the hydrolysis catalyst. The regeneration may be performed with a stream of air at at least 400° C. or alternatively with depleted air for better temperature control or else under a stream of hydrogen or a stream of ozone. Once reactivated, the catalyst is transported via a pipe 783 to the hydrolysis reactor. The gases generated during the reactivation of the hydrolysis catalyst, such as $O_2$, $CO_2$, $N_2$, CO, are evacuated via an evacuation pipe 784 of a separator 785. A hydrolysis device may correspond to a fluidized-bed hydrolysis reactor as described previously.

The reactivated catalyst is then in contact, inside the hydrolysis reactor, with the (meth)acrylate monomer derived from the depolymerization 791, and makes it possible to form (meth)acrylic acid. By means of a second separator 792, for example of cyclone type, comprising an evacuation pipe 793 for recovering the (meth)acrylic acid at the outlet of the hydrolysis reactor and a reinjection pipe 794 for reinjecting the catalyst into the hydrolysis reactor so allowing to obtain a better yield of acid. When the hydrolysis catalyst is contaminated, it is transported to the catalyst regenerating device via a pipe 795. Thus, by means of such a device for regenerating the hydrolysis catalyst outside the hydrolysis reactor, the (meth)acrylic acid yields are improved, the hydrolysis of the (meth)acrylate monomer is virtually complete and the regeneration of the hydrolysis catalyst makes it possible to reduce the costs of such a system and improves the environmental impact.

Another embodiment of the recycling system 200 is illustrated in FIG. 8. In this embodiment, the hydrolysis catalyst regenerating device may be coupled to a reactor combining hydrolysis and depolymerization. Such a reactor 810 combining hydrolysis and depolymerization is suitable for the composite article recycling system. It may include, for example, a pipe 821 suitable for introducing water into the hydrolysis reactor 810. Advantageously, the hydrolysis catalyst may be introduced into the reactor in parallel with steam or aqueous solution. The reactor comprises means 830 for introducing the article to be recycled (e.g. PMMA) which is depolymerized at high temperature to monomer of reduced molecular chain leading essentially to the formation of (meth)acrylate monomer (e.g. MMA). The monomers are then hydrolyzed, by means of the presence of steam and advantageously by means of the presence of the hydrolysis catalyst, to methacrylic acid. The methacrylic acid can then be removed from the reactor via evacuation means 840, or conveyed to a purification step as described previously. During the depolymerization and/or hydrolysis reactions, the hydrolysis catalyst can be contaminated. Thus, the contaminated catalyst is transported in a catalyst regenerating device 850 via a transportation means 860, for instance a pipe. In order to reactivate the hydrolysis catalyst, a regenerative substance 870 is introduced via introduction means 880 into the regenerator, for instance a stream of air for reactivating the hydrolysis catalyst. The regenerator comprises means 890 for evacuating the gases generated during the decontamination of the hydrolysis catalyst, and means 861 for reinjecting the catalyst into the depolymerization and hydrolysis reactor. Thus, the catalyst may be reused for several hydrolysis cycles.

Thus, the invention provides a simple and efficient solution for recycling articles based on (meth)acrylic polymers. In addition, the process according to the invention enables the specific depolymerization of polymer, while at the same time enabling saving in energy. The invention thus falls within a context of sustainable development and the upgrading of (meth)acrylic thermoplastic resin waste.

EXAMPLES

Example

Simultaneous Depolymerization and Hydrolysis of PMMA to Methacrylic Acid

A rotary fluidized-bed reactor is designed to perform the PMMA depolymerization-hydrolysis reaction. This experimental reactor has an inside diameter of 30 cm. At its base, it consists of a burner and steam injection system, on which is mounted a distribution grate and the reaction zone. This reaction zone contains a central cone and, at the top part, a side (tangential) outlet for removing the solid. At the top of the reactor, a cyclone enables the separation of the solid fines, which are returned into the reactor, and the gas which is withdrawn from the reactor.

In the lower part of the reactor, a toric distributor conveys steam under the distribution grate. In the central part of this lower zone (below the distribution grate), a gas burner makes it possible to raise the temperature of the gas and of the injected steam.

The distribution grate consists of fin tubes inclined at an angle of 23° relative to the horizontal. This inclination imposes a rotational motion on the gaseous stream, which itself places in rotation the solid which is in the reaction zone. The central cone has an outside diameter of 24 cm at its base and a height of 24 cm. The distribution grate is thus in the peripheral part of the reaction zone and the fin tubes have a width of 3 cm. The fin tubes overlap partially to clearly impose a rotational motion. The fin tubes may be articulated, i.e. the angle may be adjusted. Among other advantages, this enables the experimental reactor to be emptied more easily by gravity. This also enables the functioning of the reactor to be adjusted.

The reactor is fed with solid in its central part. The solid is fed via the top of the reactor and it falls onto the tip of the cone which is at the base of the reaction zone. The solid is thus thoroughly distributed over the fluidized bed. Two solid inlets are provided, one for the PMMA granules (or crushed PMMA) and the other for feeding in the solid catalyst.

The fluidization gas, consisting of steam and hot air coming from the gas burner, is introduced into the reaction zone via the fin tubes of the distribution grate. The rotational motion of the gas generates a centrifugal force in the bed of solid which keeps the solid in the reaction zone. On rising in the reaction zone, the passage cross section increases due to the presence of the central cone. The heaviest solids thus fall back into the bed. The fines or the lightest particles continue their gradual ascent. Between 0 and 15 cm above the tip of the central cone, a tangential solid outlet is provided. This solid evacuation may be partly blocked, which makes it possible to select the height at which the solid will be withdrawn. The extraction zone is a rectangle 5 cm tall by 1 cm wide (and adjustable in width between 1 mm and 10 mm) and which is mobile.

The solid which is withdrawn is essentially catalyst, but also contains non-depolymerized PMMA and also mineral and organic fillers which were initially present in the PMMA granules/milled material. In the experimental reactor, this solid is recovered and analyzed. In industrial functioning, the solid would be directed toward a reactor where the carbon-based residues would be burnt to heat the catalyst and the mineral fillers would be separated from the catalyst before it is returned hot into the reactor.

In the upper part of the reactor, a cyclone makes it possible to return the solids to the center of the reactor. The reaction gases are then directed toward a condenser. On the laboratory installation, the condenser is of tube-calender type and is cooled with cold water (25° C.) counter-currentwise. Immediately after condensation, the reaction products are placed in contact with an aqueous solution containing a polymerization inhibitor. At the end of the test, the aqueous solution is decanted off and the two fractions are analyzed.

In the top part of the reactor, the two solids (catalyst and PMMA granules/milled material) are injected separately. The PMMA is injected at room temperature. The catalyst is preheated to simulate the return of solid after combustion of the residual organic fractions. The temperature of the catalyst may be adjusted. The typical temperature of the catalyst entering the reactor is 550° C. when it is an inorganic solid. When it is an organic solid such as an acidic resin, its temperature is lowered to not more than 100° C.

Example 1

According to the Invention

The PMMA used in the test consists of pink colored PMMA granules of the type V826 from Altuglas, about 3 mm in size. The catalyst selected is an alumina from Condea such as Puralox SCCA 5/200 of 193 m²/g, and having a mean particle diameter of 100 microns. It is mixed with sand (washed and dried beforehand) in a proportion of 50 g of catalyst per 450 g of sand.

The reactor is fed with the catalyst preheated to 550° C., with a flow rate of mixture of catalyst and sand of 0.5 kg/h. The PMMA granules are also fed in at room temperature at a flow rate of 17 g/min. The flow rate of steam is set at 0.9 kg/h and the flow rate of combustion gas is 150 mol/h (i.e. about 4.2 kg/h). The temperature of the combustion gas and steam entering the reaction zone is adjusted to 575° C.

The degree of conversion of the PMMA is 90%. The temperature of the outlet gases is 400° C. The yield of methacrylic acid calculated on the amount of PMMA introduced is 62% by weight.

Comparative Example 2

Example 1 is repeated, but in the absence of catalyst. The yield of methacrylic acid is 2% by weight.

Comparative Example 3

Example 1 is repeated, but using an Amberlyst 15 acidic resin as catalyst, fed into the reactor at 65° C. In this configuration, the reactor is unstable. The temperature of the outlet gases is 350° C. The yield of methacrylic acid is 3% by weight.

Comparative Example 4

Example 1 is repeated using Nafion SAC from N.E. Chemcat of SAC-13 type milled to a particle size of about 200 microns.

The reactor is fed with the catalyst preheated to 80° C., with a flow rate of catalyst and sand of 1.0 kg/h. The functioning of the reactor is very unstable.

The degree of conversion of the PMMA is 70%. The temperature of the outlet gases is 330° C. The yield of methacrylic acid calculated on the amount of PMMA introduced is 3% by weight.

Comparative Example 5

The PMMA used in the test consists of pink colored PMMA granules of the type V826 from Altuglas, about 3 mm in size. The catalyst selected is an alumina from Condea such as Puralox SCCA 5/200 of 193 m²/g, and having a mean particle diameter of 100 microns. It is mixed with sand (washed and dried beforehand) in a proportion of 50 g of catalyst per 450 g of sand.

The reactor is fed with the catalyst preheated to 300° C., with a flow rate of catalyst and sand of 0.5 kg/h. The PMMA granules are also fed in at room temperature at a flow rate of 17 g/min. The flow rate of steam is set at 0.36 kg/h and the flow rate of combustion gas is 270 mol/h, i.e. about 7.7 kg/h. The temperature of the combustion gas and steam entering the reaction zone is adjusted to 300° C.

The degree of conversion of the PMMA is 20%. The temperature of the outlet gases is 190° C. In this configuration, the temperature of the gases also represents the temperature conditions present inside the reactor. The yield of methacrylic acid calculated on the amount of PMMA introduced is 15% by weight.

Example 6

According to the Invention

Example 1 is repeated, adding with the PMMA sodium perborate in a proportion of 3 g/h.

Example 7

According to the Invention

Example 6 is repeated, replacing the perborate with Luperox 101PP10, which is a solid form of 2,5-dimethyl-2,5-bis(tert-butylperoxy)hexane, in a proportion of 3 g/h.

Other reaction configuration according to the invention.

A twin-screw extruder fed with PMMA granules is used to do this. The temperature of the extruder may be adjusted by electric heating. The screw system is designed to have a first melting zone, and then a plug zone which prevents the gases from flowing back toward the feed. A port allows the injection of liquid or gas after the melting zone. At the end of the extruder, the gas produced by the reaction is directed toward a tube-calender condenser. The solid which has not depolymerized is directed toward a storage capacity kept above 100° C. The gases produced pass through a dust-removal cyclone kept hot before the condensation zone.

Example 8

According to the Invention

The extruder is fed with a flow rate of 5 kg/h of PMMA granules, and 1 kg/h of Condea alumina of Puralox SCCA 5/200 type, and also a gentle flow rate of inert gas (nitrogen). After the plug zone, the extruder is fed with an aqueous hydrogen peroxide solution containing 10% by weight of H2O2, at a flow rate of 2 kg/h. The temperature of the extruder is maintained at 350° C. The yield of methacrylic acid is 73% by weight.

Example 9

According to the Invention

The preceding example is repeated with just a flow rate of water instead of the hydrogen peroxide solution. With the PMMA granules, a solid flow rate of sodium percarbonate ($Na_2CO_3 \cdot 1.5H_2O_2$) of 0.004 kg/h is added. The yield of methacrylic acid is 65% by weight.

The invention claimed is:

1. A process for the recycling of an article based on (meth)acrylic thermoplastic polymer resin, wherein said process comprises introducing the article, a hydrolysis catalyst and water into a recycling system, the recycling system including a reactor for performing a depolymerization-hydrolysis reaction, and
   performing the depolymerization-hydrolysis reaction in the reactor, the depolymerization-hydrolysis reaction simultaneously involving
   partially depolymerizing the (meth)acrylic thermoplastic polymer resin to form (meth)acrylate monomers, and
   converting at least part of the (meth)acrylate monomers into (meth)acrylic acid.

2. The recycling process as claimed in claim 1, wherein the hydrolysis catalyst is selected from the group consisting of: alumina, MgO, CaO, $Mg(OH)_2$, $Ca(OH)_2$, $Al(OH)_3$, a zeolite, an acid, a base, an amphoteric compound and a mixture of two or more of these compounds.

3. The recycling process as claimed in claim 1, wherein the process further comprises a step of regenerating the catalyst.

4. The recycling process as claimed in claim 1, wherein the process further includes introducing a concentration of depolymerization-initiating catalyst into the recycling system.

5. The recycling process as claimed in claim 4, wherein the depolymerization-initiating catalyst is selected from the group consisting of: an organic peroxide, an inorganic peroxide, a superoxide, barium peroxide ($BaO_2$), potassium superoxide ($KO_2$), cesium superoxide ($CsO_2$), a percarbonate, a peroxyhydrate compound, salts thereof and a mixture thereof.

6. The recycling process as claimed in claim 4, wherein the depolymerization-initiating catalyst is solid at 25° C.

7. The recycling process as claimed in claim 4, wherein the depolymerization-initiating catalyst is chosen from perborates and percarbonates.

8. The recycling process as claimed in claim 4, wherein the depolymerization-initiating catalyst is sodium percarbonate.

9. The recycling process as claimed in claim 4, wherein the concentration of depolymerization-initiating catalyst is such that a mole ratio of 0.001 and 10 is formed between the depolymerization-initiating catalyst and the (meth)acrylic thermoplastic polymer present in the article.

10. The recycling process as claimed in claim 1, wherein the hydrolysis catalyst is selected from the group consisting of: alumina, MgO, CaO, $Mg(OH)_2$, $Ca(OH)_2$, $Al(OH)_3$, a zeolite, a base, an amphoteric compound and a mixture of two or more of these compounds.

11. The recycling process as claimed in claim 1, wherein the temperature of the hydrolysis catalyst, when said catalyst is an inorganic solid, is at least 300° C. when introduced into the recycling system.

12. The recycling process as claimed in claim 1, wherein the process further includes a distillation step suitable for generating a mixture enriched in (meth)acrylic acid.

13. The recycling process as claimed in claim 1, wherein the process further includes a crystallization step suitable for generating a mixture enriched in (meth)acrylic acid.

14. The recycling process as claimed in claim 1, wherein the article to be recycled is made of composite material based on (meth)acrylic thermoplastic polymer resin and a reinforcer.

15. The recycling process as claimed in claim 1, wherein the process further includes a heat recovery step.

16. The recycling process as claimed in claim 1, wherein a gas comprising steam is produced in the recycling system.

17. The recycling process as claimed in claim 1, wherein water is introduced into the recycling system as an aqueous solution.

18. The recycling process as claimed in claim 1, wherein the amount of water introduced into the recycling system is at least stoichiometric relative to the amount of (meth)acrylate monomers to be hydrolyzed.

19. The recycling process as claimed in claim 1, wherein the amount of water added into the recycling system is greater than or equal to 15% of the mass of the (meth)acrylic thermoplastic polymer present in the article.

20. The recycling process as claimed in claim 1, wherein the temperature in the reactor is between 150° C. and 250° C.

21. The recycling process as claimed in claim 1, wherein the reactor is a hydrolysis reactor or a fluidized-bed reactor.

\* \* \* \* \*